(12) United States Patent
Sato et al.

(10) Patent No.: US 10,617,328 B2
(45) Date of Patent: Apr. 14, 2020

(54) LOAD DETECTOR INCLUDING LOAD CELL AND PLATFORM CONNECTED TO LOAD CELL, AND LOAD DETECTING SYSTEM

(71) Applicant: Minebea Mitsumi Inc., Nagano (JP)

(72) Inventors: Kunihiko Sato, Fusjisawa (JP); Jun Hatcho, Kitasaku-gun (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 16/131,541

(22) Filed: Sep. 14, 2018

(65) Prior Publication Data

US 2019/0015015 A1    Jan. 17, 2019

Related U.S. Application Data

(63) Continuation of application No. PCT/JP2017/009115, filed on Mar. 8, 2017.

(30) Foreign Application Priority Data

Mar. 16, 2016 (JP) ................................. 2016-052656

(51) Int. Cl.
*A61B 5/11* (2006.01)
*A61G 7/05* (2006.01)
(Continued)

(52) U.S. Cl.
CPC .......... *A61B 5/1115* (2013.01); *A61B 5/6892* (2013.01); *A61G 7/05* (2013.01);
(Continued)

(58) Field of Classification Search
CPC .......... G01G 3/14; G01G 19/02; G01G 19/44; G01G 19/445; G01G 19/52; G01G 21/18;
(Continued)

(56) References Cited

U.S. PATENT DOCUMENTS 3,691,675 A * 9/1972 Rodgers ................. A63H 13/16
446/188
4,281,730 A * 8/1981 Swersey ............... G01G 19/445
177/144
(Continued)

FOREIGN PATENT DOCUMENTS

CN          201068294 Y     6/2008
CN          201163214 Y    12/2008
(Continued)

OTHER PUBLICATIONS

English translation of the Written Opinion for International Application No. PCT/JP2017/009115 dated Apr. 25, 2017.
(Continued)

*Primary Examiner* — Randy W Gibson
(74) *Attorney, Agent, or Firm* — Pearne & Gordon LLP

(57) ABSTRACT

There is provided a load detector including a beam-type load cell which is supported on a support base in a cantilever manner, and a platform connected to the beam-type load cell. The platform includes a main body on which a subject is to be placed and a slope having a first end, which is connected to the main body, the slope being configured to guide the subject to the main body. The slope is configured to swing between a first position in which a second end of the slope is in contact with a placement surface on which the load detector is placed and a second position in which the second end is separated from the placement surface. The platform further includes a lever connected to the first end of the slope and positioned above the main body.

22 Claims, 16 Drawing Sheets

(51) Int. Cl.
*G01G 19/44* (2006.01)
*G01G 19/02* (2006.01)
*G01G 21/28* (2006.01)
*G01G 21/18* (2006.01)
*G01G 3/14* (2006.01)
*A61B 5/00* (2006.01)

(52) U.S. Cl.
CPC ............... *G01G 3/14* (2013.01); *G01G 19/02* (2013.01); *G01G 19/44* (2013.01); *G01G 19/445* (2013.01); *G01G 21/18* (2013.01); *G01G 21/28* (2013.01)

(58) Field of Classification Search
CPC ..... G01G 21/28; A61B 5/6892; A61B 5/1115; A61G 7/05
See application file for complete search history.

(56) References Cited

U.S. PATENT DOCUMENTS

| | | | | |
|---|---|---|---|---|
| 5,086,856 A * | 2/1992 | Haggstrom | ......... | G01G 19/445 177/1 |
| 5,367,129 A | 11/1994 | Lahl, Jr. | | |
| 6,380,496 B1 * | 4/2002 | Lohkamp | ............ | G01G 19/445 177/144 |
| 6,717,072 B1 * | 4/2004 | Winterberg | ......... | G01G 19/445 177/126 |
| 6,765,154 B2 * | 7/2004 | Sternberg | ............ | G01G 19/445 177/126 |
| 7,511,234 B1 * | 3/2009 | Ebinger | ............... | G01G 19/021 177/132 |
| 7,589,288 B2 * | 9/2009 | Wu | ......................... | G01G 3/14 177/144 |
| 7,795,548 B2 * | 9/2010 | Woods | .................. | G01G 19/56 177/131 |
| 7,838,782 B2 * | 11/2010 | Hamilton | .............. | G01M 1/125 177/132 |
| 2008/0272137 A1 | 11/2008 | Fitzgerald et al. | | |

FOREIGN PATENT DOCUMENTS

| | | |
|---|---|---|
| JP | 2005-300368 A | 10/2005 |
| JP | 4120094 B1 | 7/2008 |

OTHER PUBLICATIONS

International Preliminary Report on Patentability for International Application No. PCT/JP2017/009115 dated Sep. 18, 2018.
International Search Report for International Application No. PCT/JP2017/009115 dated Apr. 25, 2017.
Notice of Reasons for Rejection dated Sep. 26, 2016 for corresponding Japanese Application No. 2016-052656 and partial English translation.
Chinese office Action dated Aug. 14, 2019 for corresponding Chinese Application No. 201780017519.2 and English translation.
Chinese office Action dated Feb. 18, 2019 for corresponding Chinese Application No. 201780017519.2 and English translation.
Extended European Search Report dated Feb. 15, 2019 for corresponding European Application No. 17766471.1.
European Office Action dated Nov. 20, 2019 for corresponding European Application No. 17766471.1.
Decision of Rejection dated Dec. 27, 2019 for corresponding Chinese Application No. 201780017519.2 and English translation.

\* cited by examiner

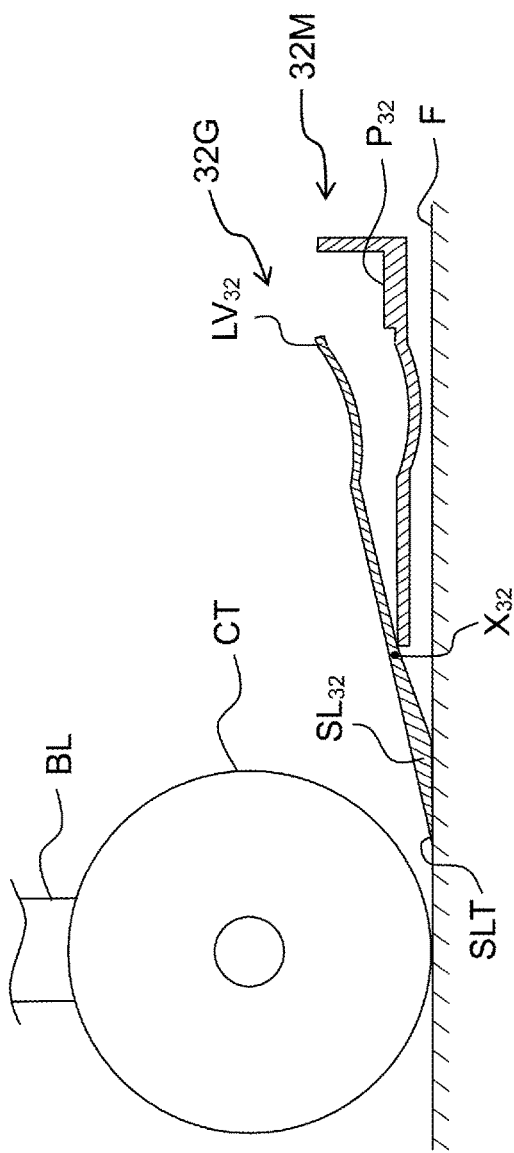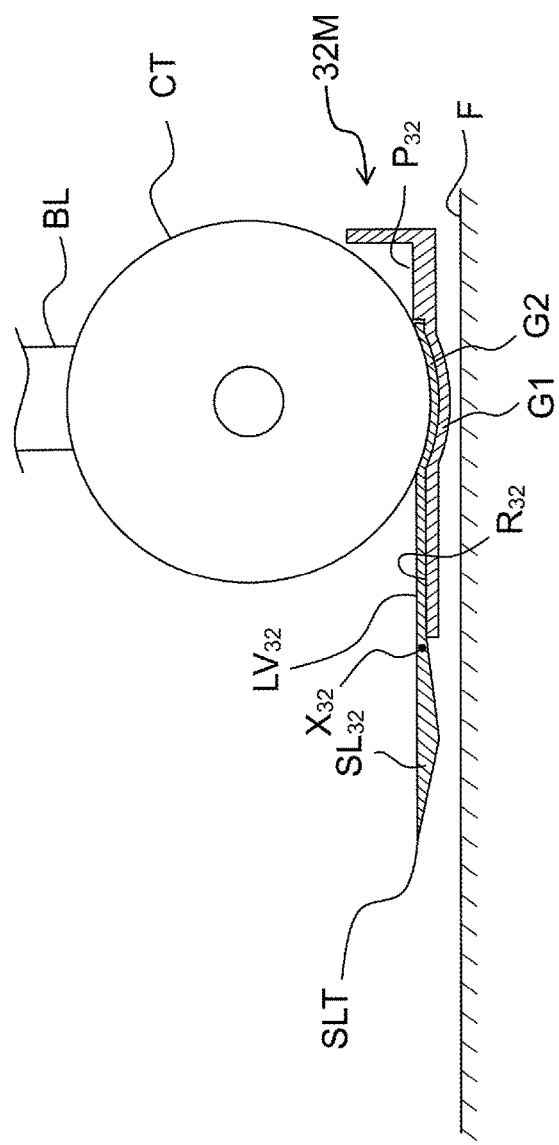
Fig. 11A
Fig. 11B

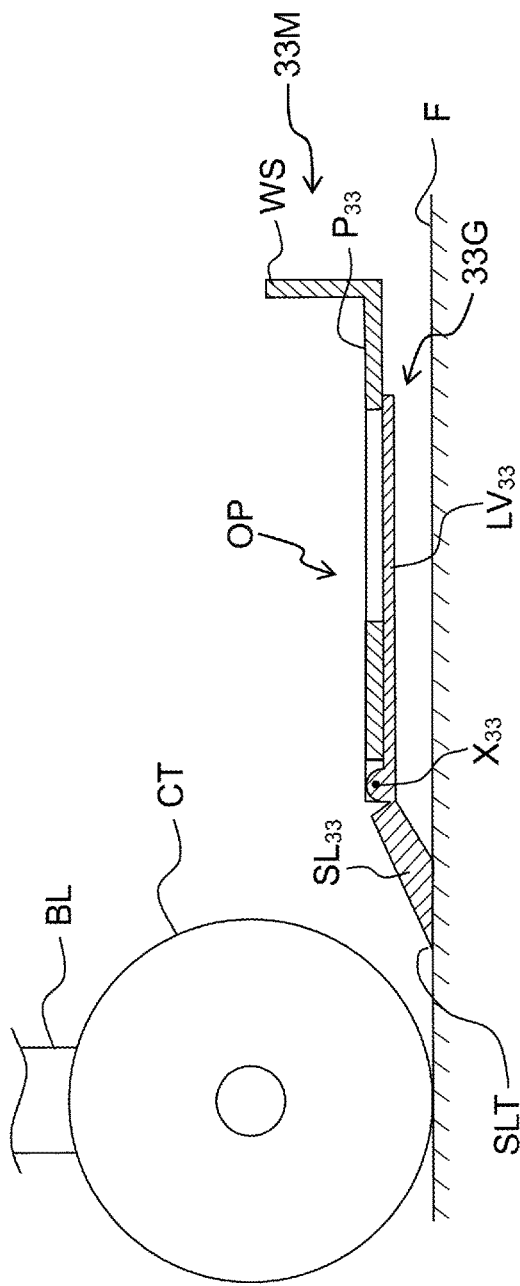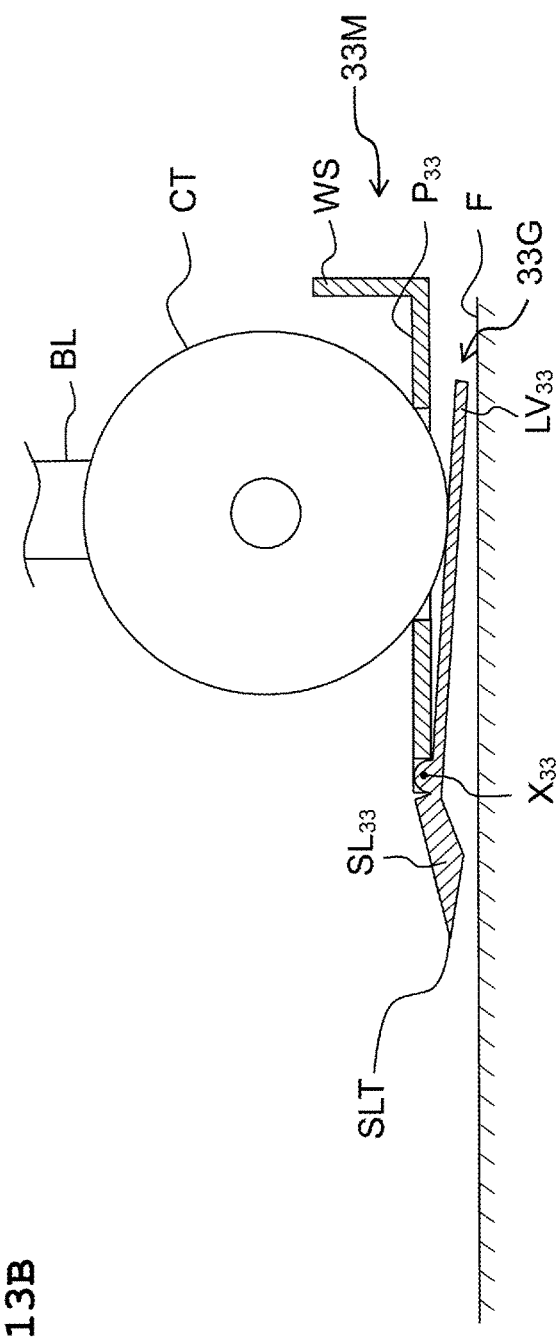

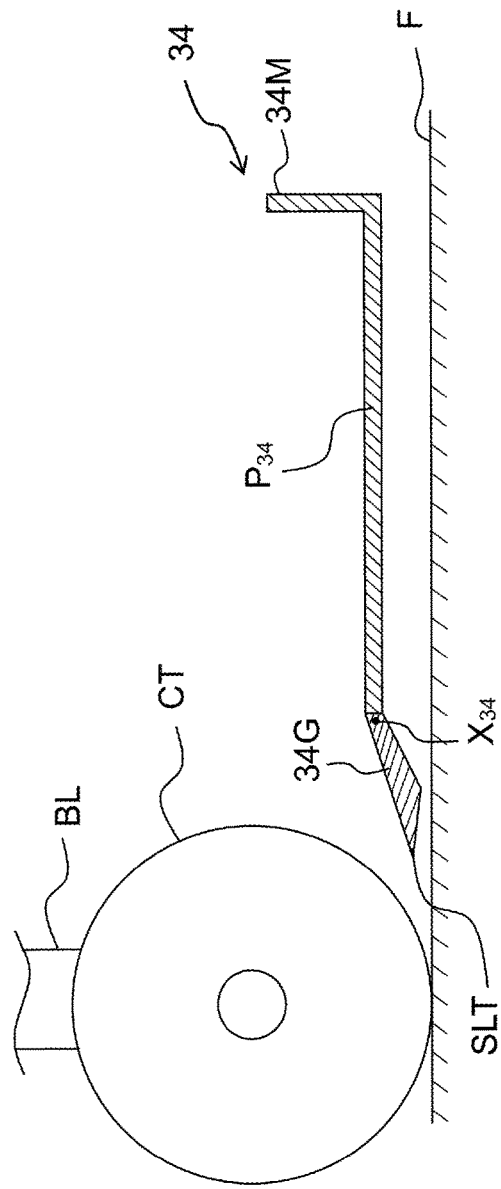
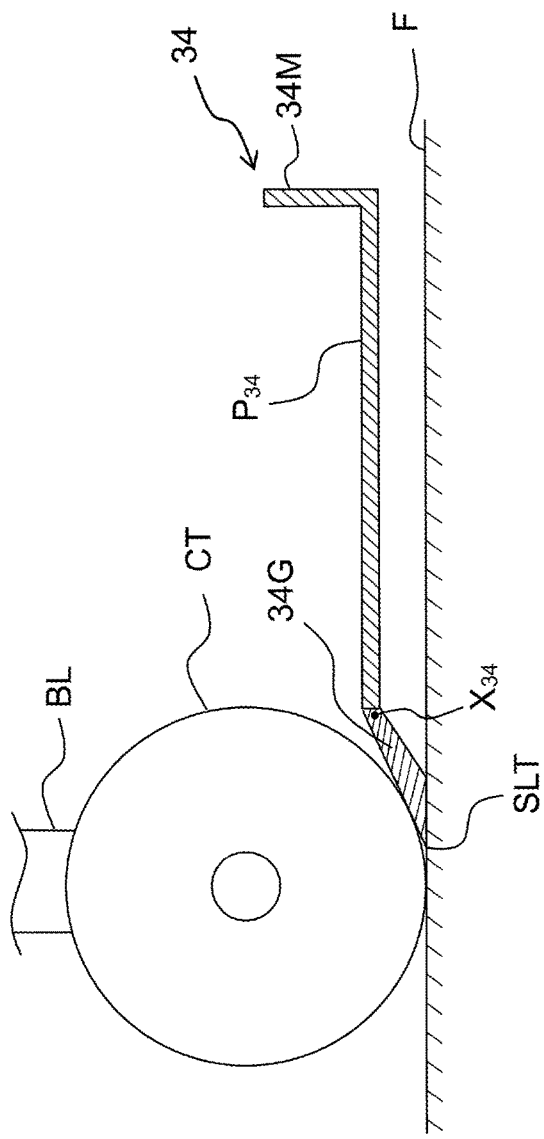
Fig. 15A
Fig. 15B

LOAD DETECTOR INCLUDING LOAD CELL AND PLATFORM CONNECTED TO LOAD CELL, AND LOAD DETECTING SYSTEM

CROSS-REFERENCE TO RELATED APPLICATIONS

This application is a Continuation Application of International Application No. PCT/JP2017/009115 claiming the conventional priority of Japanese patent Application No. 2016-052656 filed on Mar. 16, 2016, and titled "LOAD DETECTOR AND LOAD DETECTING SYSTEM". The disclosures of Japanese patent Application No. 2016-052656, and International Application No. PCT/JP2017/009115 are incorporated herein by reference in their entirety.

BACKGROUND

The present disclosure relates to a load detector provided with a platform (placement platform, mounting stand) that includes a swingable slope, and a load detecting system (load detection system) including the load detector.

There is known present-on-bed detection in which a load applied to a bed in hospitals, nursing homes, and the like is detected to determine whether a patient or an assisted-living resident is present on the bed. The detection of the load can be performed by disposing load detectors at various positions, and Japanese Patent Application Laid-open No. 2005-300368 discloses, as its example, arranging a load detector under each support leg supporting a bed.

SUMMARY

It is desired that the load detector can be placed under an object to be detected (load detection target) more easily, such as easier placement of the load detector under each support leg supporting a bed. Although Japanese Patent Application Laid-open No. 2005-300368 describes that a heavy load, such as a bed, is placed on a measuring pan of a load scale, the simplicity and easiness of placement is not enough. Meanwhile, the load detector is desired to prevent or reduce a measurement error during load detection.

An object of the present disclosure is thus to provide a load detector that allows an object to be detected (detection object, detection target) to be easily placed thereon and is capable of preventing or reducing a measurement error, and a load detection system including the load detector.

According to a first aspect of the present disclosure, there is provided a load detector, including:

a beam-type load cell which is supported on a support base in a cantilever manner; and a platform connected to the beam-type load cell, wherein the platform includes a main body on which a subject is to be placed and a slope having a first end, which is connected to the main body, the slope being configured to guide the subject to the main body, the slope is configured to swing between a first position in which a second end of the slope is in contact with a placement surface on which the load detector is placed and a second position in which the second end is separated from the placement surface, and the platform further includes a lever connected to the first end of the slope and positioned above the main body.

According to a second aspect of the present disclosure, there is provided a load detector, including:

a beam-type load cell which is supported on a support base in a cantilever manner; and a platform connected to the beam-type load cell, wherein the platform includes a main body on which a subject is to be placed and a slope having a first end, which is connected to the main body, the slope being configured to guide the subject to the main body, the slope is configured to swing between a first position in which a second end of the slope is in contact with a placement surface on which the load detector is placed and a second position in which the second end is separated from the placement surface, the main body includes an opening, and the platform further includes a lever connected to the first end of the slope and disposed below the main body to cover the opening.

According to a third aspect of the present disclosure, there is provided a load detector, including:

a beam-type load cell which is supported on a support base in a cantilever manner; and a platform connected to the beam-type load cell, wherein the platform includes a main body on which a subject is to be placed and a slope having a first end, which is connected to the main body, the slope being configured to guide the subject to the main body, the slope is configured to swing between a first position in which a second end of the slope is in contact with a placement surface on which the load detector is placed and a second position in which the second end is separated from the placement surface, the beam-type load cell includes a first beam-type load cell which is supported on a first support base in a cantilever manner to have a free end and a second beam-type load cell which is disposed to face the first beam-type load cell and which is supported on a second support base in a cantilever manner to have a free end, the platform is provided between the first beam-type load cell and the second beam-type load cell and further includes a first connection part connected to the first beam-type load cell and a second connection part connected to the second beam-type load cell, the free end of the first beam-type load cell and the free end of the second beam-type load cell face opposite directions to each other in an extending direction of the first beam-type load cell, and the first connection part of the platform is connected to the first beam-type load cell on a side of the free end of the first beam-type load cell and the second connection part of the platform is connected to the second beam-type load cell on a side of the free end of the second beam-type load cell.

According to a fourth aspect of the present disclosure, there is provided a load detection system configured to detect a load of a human subject on a bed, the system including:

a plurality of load detectors each of which is the load detector of any one of the first to third aspects, the plurality of load detectors being disposed under legs of the bed, respectively; and a controller connected to the plurality of load detectors and configured to calculate the load of the human subject based on an output of the load detector.

BRIEF DESCRIPTION OF DRAWINGS

FIG. 11A depicts placement of the caster on the platform according to the second embodiment of the present disclosure, in particular, a situation before the caster is placed on the platform, and FIG. 11B depicts placement of the caster on the platform according to the second embodiment of the present disclosure, in particular, a situation after the caster is placed on the platform.

FIG. 13A depicts placement of the caster on the platform according to the second modified example of the present disclosure, in particular, a situation before the caster is placed on the platform, and FIG. 13B depicts placement of the caster on the platform according to the second modified example of the present disclosure, in particular, a situation after the caster is placed on the platform.

FIG. 15A depicts placement of the caster on the platform according to the third modified example of the present disclosure, in particular, a situation before the caster is placed on the platform, and FIG. 15B depicts placement of the caster on the platform according to the third modified example of the present disclosure, in particular, a situation in which the caster is positioned on a slope.

EMBODIMENTS

First Embodiment

Referring FIGS. 1 to 7, a load detector 100 according to a first embodiment of the present disclosure is explained. In the first embodiment, the load detector 100 is a load detector that is disposed under a leg BL (FIGS. 4A and 4B) of a bed to detect a load of a human subject (subject) on the bed.

Figure 1:
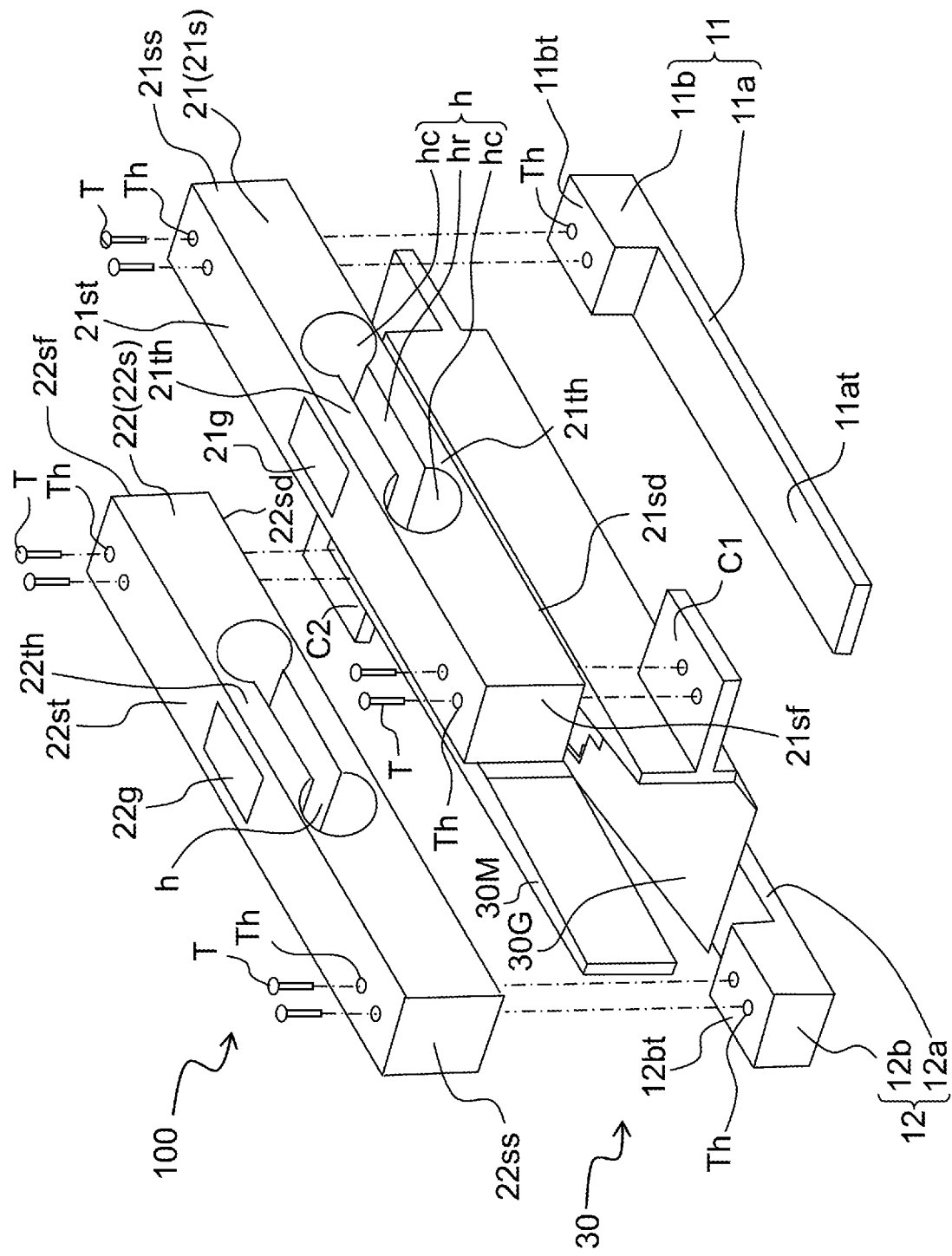
FIG. 1 is an exploded perspective view of a load detector according to a first embodiment of the present disclosure.
Figure 2:
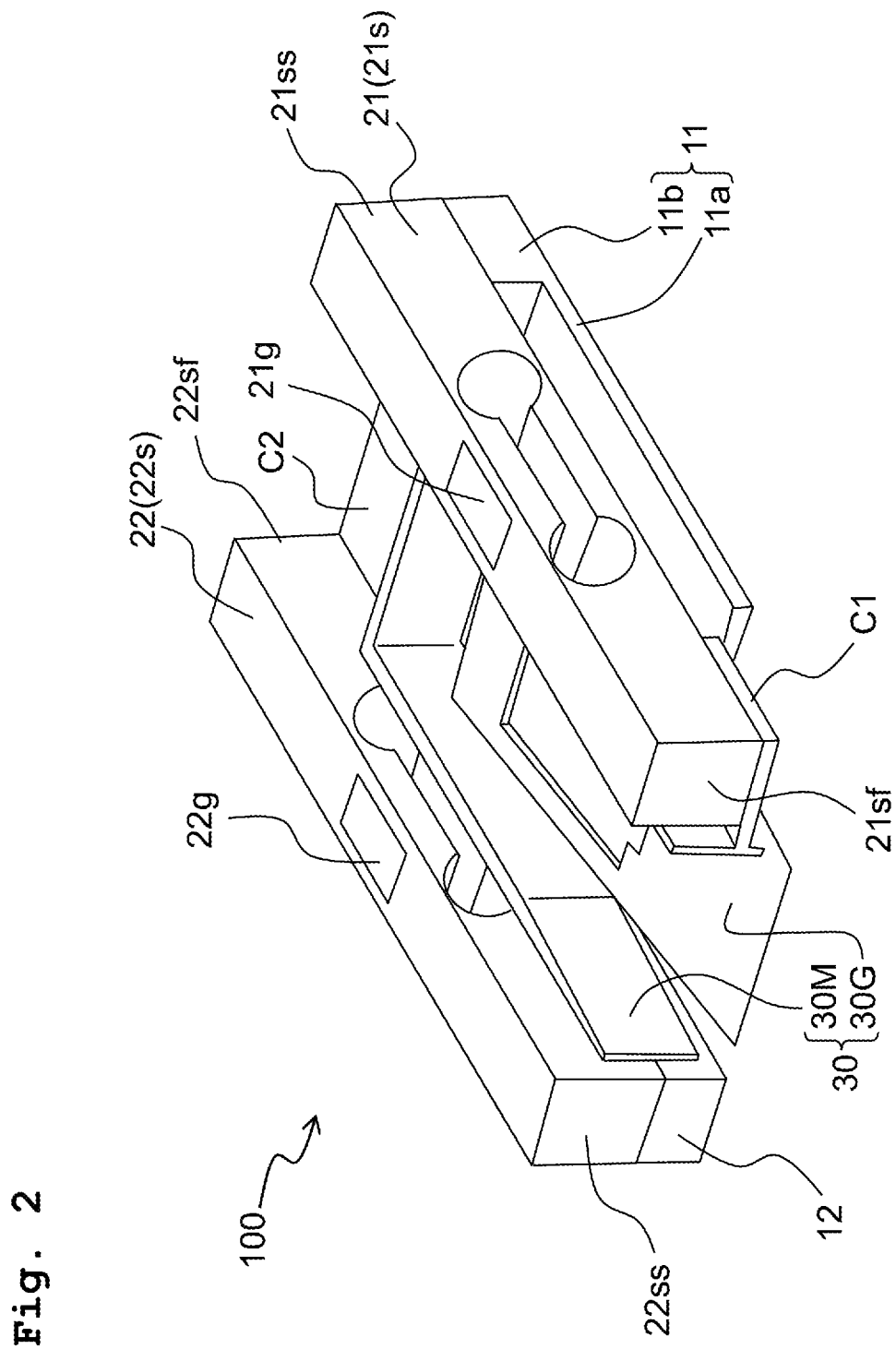
FIG. 2 is a perspective view of the load detector according to the first embodiment of the present disclosure.

As depicted in FIGS. 1 and 2, the load detector 100 mainly includes a first base 11, a second base 12, a first load cell 21 of a beam type that is connected to the first base 11, a second load cell 22 of a beam type that is connected to the second base 12, and a platform (mounting part) 30 that is supported by the first and second load cells 21, 22 to be positioned therebetween. In the following, a direction in which beams of the beam-type first and second load cells 21, 22 extend is defined as a longitudinal direction. A surface on which the load detector 100 is placed is referred to as a floor.

The first base 11 is a member disposed on the floor to support the first load cell 21 in a cantilever manner. The first base 11 includes a flat plate 11a, of which planar shape is a rectangle almost identical to the planer shape of the first load cell 21, and a support base part 11b that extends upward from an end of the flat plate 11a. Atop surface 11bt of the support base part 11b is positioned above a top surface 11at of the flat plate 11a.

The top surface 11bt of the support base part 11b includes two screw holes Th. The first load cell 21 is fixed to the support base part 11b via screws T and the screw holes Th.

The second base 12, which has the same shape as the first base 11, includes a flat plate 12a and a support base part 12b. The second base 12 is disposed to face the first base 11 (to be parallel to the first base 11 in the first embodiment) with a predefined distance intervening therebetween, and the support base part 11b of the first base 11 is positioned on a side opposite to the side on which the support base part 12b is positioned. Namely, the support base part 11b is connected to the flat plate 11a of the first base 11 on a side opposite to the side on which the support base part 12b is connected to the flat plate 12a of the second base 12, in the longitudinal direction. The second load cell 22 is fixed to the support base part 12b via screws T and screw holes Th formed in the top surface 12bt of the support base part 12b.

The first load cell 21, which is a beam-type load cell, includes a flexure element (strain body) 21s in a rectangular column shape that has a through hole h, and a strain gage 21g attached on the flexure element 21s. The first load cell 21 detects the strain or distortion generated in the flexure element 21s as the change in a resistance value of the strain gage 21g. Accordingly, the load applied to the first load cell 21 is detected.

The flexure element 21s is a long square pillar made of metal such as aluminum or iron. The through hole h, which passes through the flexure element 21s in the width direction, is formed in the center portion in the longitudinal direction of the flexure element 21s. The through hole h includes two circular holes hc and a rectangular hole hr. Each of the circular holes hc has a circular cross-sectional shape, and the rectangular hole hr, which has a substantially rectangular cross-sectional shape, connects the two circular holes hc to each other in the longitudinal direction. Parts, of the flexure element 21s, positioned on the upper and lower sides of the through hole h are thin parts 21th that are thinner in the up-down direction due to existence of the through hole h.

Two screw holes Th passing through the flexure element 21s in the up-down direction are formed in the vicinity of a first end 21ss of the flexure element 21s. The first end 21ss of the flexure element 21s is fixed to the support base part 11b of the first base 11 via screws T and the screw holes Th. This allows the flexure element 21s to be supported by the first base 11 (support base part 11b) in a cantilever manner with the first end 21ss being a fixed end, the second end 21sf being a free end.

Further, two screw holes Th passing through the flexure element 21s in the up-down direction are formed in the vicinity of the second end 21sf of the flexure element 21s. The platform 30 is fixed to a lower surface 21sd of the flexure element 21s in the vicinity of the second end 21sf via the screws T and the screw holes Th. Namely, the flexure element 21s (first load cell 21) supports the platform 30 in the vicinity of the second end 21sf as the free end so that the platform 30 is movable in the up-down direction.

Two strain gages 21g are attached to the thin parts 21th of the flexure element 21s. Specifically, one of the two strain gages 21g is attached to an upper surface 21st of the flexure element 21s and the other of the two strain gages 21g is attached to the lower surface 21sd of the flexure element 21s, at the substantially center portion in the longitudinal direction of the flexure element 21s. The strain gages 21g are connected to an external controller via unillustrated lead wires.

The second load cell 22, which has the same structure as the first load cell 21, includes a flexure element (strain body) 22s in a rectangular column-shape and two strain gages 22g. The flexure element 22s includes a through hole h passing through the center portion of the flexure element 22s in the width direction. Each of the strain gages 22g is attached to the corresponding one of thin parts 22th of the flexure element 22s. The second load cell 22 is disposed to face the first load cell 21 (to be parallel to the first load cell 21 in first embodiment) with a predefined distance intervening therebetween.

Two screw holes Th passing through the flexure element 22s in the up-down direction are formed in the vicinity of a first end 22ss of the flexure element 22s. The first end 22ss of the flexure element 22s is fixed to the support base part 12b of the second base 12 via screws T and the screw holes Th. This allows the flexure element 22s to be supported by the second base 12 (support base part 12b) in a cantilever manner with the first end 22ss being a fixed end, a second end 22sf being a free end.

Further, two screw holes Th passing through the flexure element 22s in the up-down direction are formed in the vicinity of the second end 22sf of the flexure element 22s. The platform 30 is fixed to a lower surface 22sd of the flexure element 22s in the vicinity of the second end 22sf via screws T and the screw holes Th. Namely, the flexure element 22s (second load cell 22) supports the platform 30 in the vicinity of the second end 22sf as the free end so that the platform 30 is movable in the up-down direction. In the arrangement relation between the flexure element 21s and the flexure element 22s, the first end (fixed end) 22ss of the flexure element 22s is in the same position, in the longitudinal direction, as the second end (free end) 21sf of the flexure element 21s, and the second end (free end) 22sf of the flexure element 22s is in the same position, in the longitudinal direction, as the first end (fixed end) 21ss of the flexure element 21s. Namely, the flexure element 21s and the flexure element 22s extend in the same direction while facing each other, and the fixed end and the free end of the flexure element 21s are positioned reversely to the fixed end and the free end of the flexure element 22s in the longitudinal direction. Further, the support base part 11b supporting the flexure element 21s is in substantially the same position as the second end (free end) 22sf of the flexure element 22s in the longitudinal direction, and the support base part 12b supporting the flexure element 22s is in substantially the same position as the second end (free end) 21sf of the flexure element 21s in the longitudinal direction.

Figure 3:
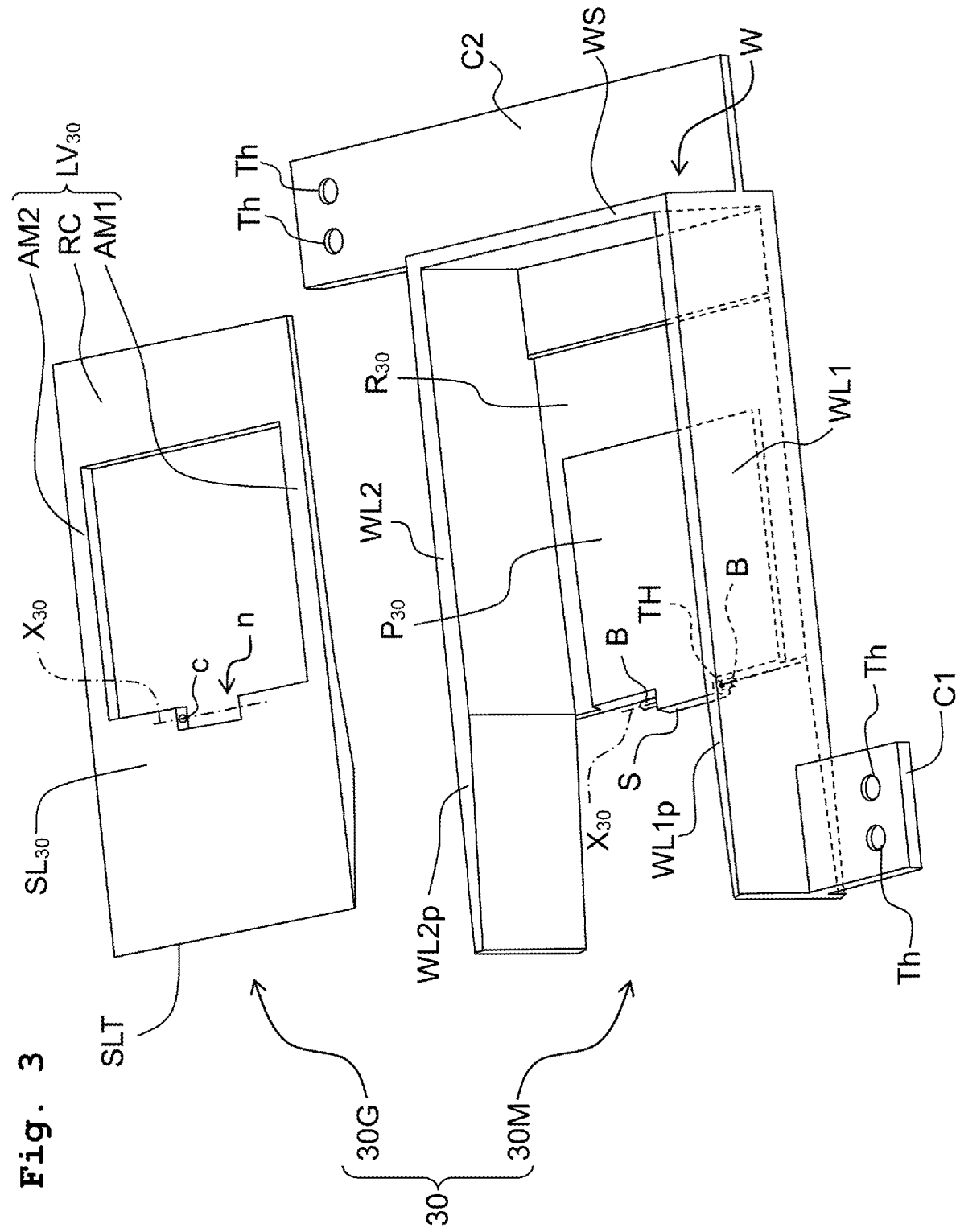
FIG. 3 is an exploded perspective view of a platform included in the load detector according to the first embodiment of the present disclosure.

The platform 30 is a platform on which an object to be detected (detection object, detection target) is placed when a load of the detection target is to be detected by the load detector 100. As depicted in FIG. 3, the platform 30 includes a main body 30M and a guide 30G that is attached to the main body 30M so that the guide 30G moves swingably (moves like a seesaw, or moves pivotally).

The main body 30M includes a rectangular plate $P_{30}$ on which the detection target is placed, a wall W surrounding the plate $P_{30}$ on three sides thereof, and a first connection part C1 and a second connection part C2 that are provided in the wall W. The first and second connection parts C1 and C2 are provided in the wall W. A side, on which the detection target described below is placed, relative to the plate $P_{30}$ is defined as the upper side of the main body 30M and the plate $P_{30}$ (above the main body 30M and the plate $P_{30}$), and its opposite side is defined as the lower side of the main body 30M and the plate $P_{30}$ (below the main body 30M and the plate $P_{30}$).

A recess $R_{30}$, which has substantially a C-shape or U-shape in plan view, is provided in the upper surface of the plate $P_{30}$. The recess $R_{30}$ is formed so that an opening portion of the C-shape (U-shape) is positioned on one side in the long-side direction of the plate $P_{30}$ (on a side having no wall W).

One of short sides of the plate $P_{30}$ not having the wall W is provided with a shaft support part S, which has a rectangular parallelepiped shape and disposed at the center portion of the short side. The shaft support part S is provided with bosses B protruding toward both sides in the short-side direction of the plate $P_{30}$.

The wall W, which is perpendicular (orthogonal) to the plate $P_{30}$, includes a first long wall WL1 extending along one of the long sides of the plate $P_{30}$, a second long wall WL2 extending along the other of the long sides of the plate $P_{30}$, and a short wall WS extending along one of the short sides of the plate $P_{30}$ and connecting the first long wall WL1 and the second long wall WL2.

Ends, of the first long wall WL1 and the second long wall WL2, opposite to ends connected to the short wall WS protrude beyond the plate $P_{30}$. In the following, a protruding portion of the first long wall WL1 is referred to as a first protrusion WL1p, and a protruding portion of the second long wall WL2 is referred to as a second protrusion WL2p. The inner surfaces, of the first protrusion WL1p and the second protrusion WL2p, facing each other are tapered so that a distance between the inner surfaces are longer as the inner surfaces are further separated from the plate $P_{30}$ in the long-side direction of the plate $P_{30}$.

The first connection part C1, which has a plate-like shape and is parallel to the plate $P_{30}$, is provided in the outer surface of the first protrusion WL1p. The first connection part C1, which has a substantially square shape in plan view, has two screw holes Th at substantially the center portion. The first connection part C1 is fixed to the lower surface 21sd of the flexure element 21s of the first load cell 21 in the vicinity of the second end (free end) 21sf of the flexure element 21s via the screws T and the screw holes Th (FIGS. 1 and 2).

The outer surface, of the short wall WS, facing a side opposite to the side on which the plate $P_{30}$ is positioned is provided with the second connection part C2 having a plate-like shape and being parallel to the plate $P_{30}$. The second connection part C2 has a rectangular shape of which longitudinal direction is the extending direction of the short wall WS. An end in the longitudinal direction of the second connection part C2 extends beyond the second long wall WL2. The portion extending beyond the second long wall WL2 has two screw holes Th. The second connection part C2 is fixed to the lower surface $22sd$ of the flexure element $22s$ of the second load cell 22 in the vicinity of the second end (free end) $22sf$ of the flexure element $22s$ via the screws T and the screw holes Th (FIGS. 1 and 2). As depicted in FIGS. 2 and 3, the screw holes Th of the first connection part C1 and the screw holes Th of the second connection part C2 are arranged with the plate $P_{30}$ intervening therebetween in the diagonal direction.

The guide 30G which has a plate-like shape, includes a slope $SL_{30}$ and a lever $LV_{30}$ connected integrally with the slope $SL_{30}$.

The slope $SL_{30}$ has substantially a rectangular shape in plan view. The upper surface of the slope $SL_{30}$ defines an inclined surface (slope) for moving a rolling body (e.g., a caster CT) from the floor onto the platform 30. In the slope $SL_{30}$, a notch n, which has substantially a rectangular shape in plan view, is defined at the center portion of a long side (a first end) to which the lever $LV_{30}$ is connected. Surfaces facing each other and defining short sides of the notch n respectively include recessed holes c. The slope $SL_{30}$ is thicker than the lever $LV_{30}$ (see FIGS. 3, 4A, and 4B). The slope $SL_{30}$ is tapered toward a front end SLT (a second end).

The lever $LV_{30}$ is an extending part that extends from the first end of the slope $SL_{30}$ toward an opposite side of the front end SLT. The lever $LV_{30}$ includes a first arm AM1 and a second arm AM2 which are connected to ends of the long sides of the rectangular slope $SL_{30}$, and a rectangular part (contact part) RC that is disposed on an opposite side of the slope $SL_{30}$ and connected to the first arm AM1 and the second arm AM2. The lever $LV_{30}$ has substantially a C-shape (U-shape) in plan view.

The guide 30G is attached to the main body 30M so that the guide 30G can move swingably. Specifically, fitting the bosses B of the shaft support part S of the plate $P_{30}$ into the recessed holes c of the notch n of the slope $SL_{30}$ allows the guide 30G to be connected to the main body 30M so that the guide 30G seesaws (swings) around a swing shaft $X_{30}$ connecting the bosses B and the recessed holes c. The guide 30G is configured so that weight of the front side of the recessed holes c (a side close to the front end SLT of the slope $SL_{30}$) is greater than weight of the rear side of the recessed holes c (a side close to the lever $LV_{30}$) by differentiating the thickness and structure of the slope $SL_{30}$ from those of the lever $LV_{30}$, in the extending direction of the guide 30G. In that configuration, the guide 30G moves like a seesaw, with the swing shaft $X_{30}$ as the center, in a direction in which the front end SLT moves down, when no load is applied to the lever $LV_{30}$. This makes the front end SLT contact with the floor. Instead of the configuration in which the front end SLT side of the slope $SL_{30}$ is heavier than the lever $LV_{30}$ side of the slope $SL_{30}$, the slope $SL_{30}$ may include a mechanism that urges (biases) the front end SLT with a spring, a magnet, or the like toward the floor.

Figure 4A:
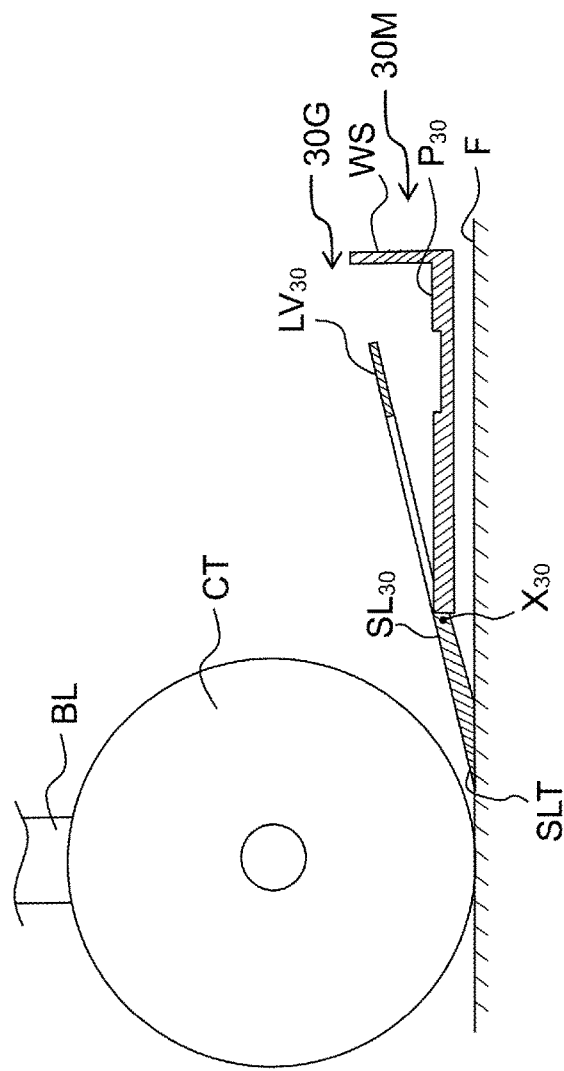
FIG. 4A depicts placement of a caster on the platform, in particular, a situation before the caster is placed on the platform.
Figure 4B:
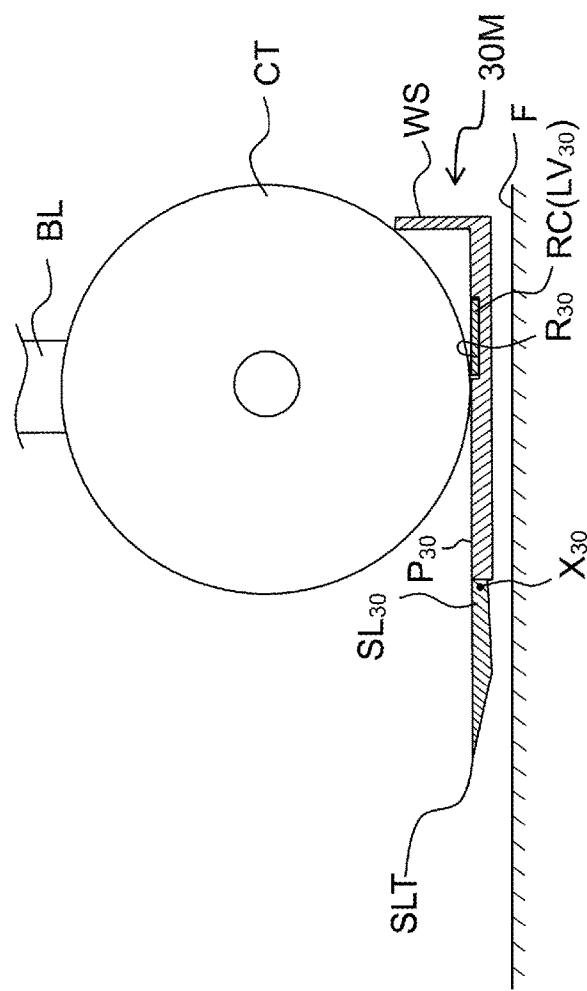
FIG. 4B depicts placement of the caster on the platform, in particular, a situation after the caster is placed on the platform.

The shape of the recess $R_{30}$ of the plate $P_{30}$ of the main body 30M in plan view is substantially the same as the shape of the lever $LV_{30}$ of the guide 30G in plan view. In that configuration, when the guide 30G moves like a seesaw relative to the main body 30M to make lever $LV_{30}$ of the guide 30G contact with the plate $P_{30}$ of the main body 30M, the lever $LV_{30}$ is disposed in the recess $R_{30}$ (FIG. 4B). Here, the upper surface of the lever $LV_{30}$ may be flush with the upper surface of the plate $P_{30}$.

Subsequently, explanation is made about a method for using the load detector 100 by citing, as its example, a case in which the detection target is a human subject on a bed and the caster CT for moving the bed, which is attached to the lower end of the leg BL (FIGS. 4A and 4B) of the bed, is placed on the platform 30. In that case, the caster CT is also the detection target (subject).

When the load detection using the load detector 100 is performed, at first, the caster CT is placed on the plate $P_{30}$ of the main body 30M of the platform 30. In a state where the caster CT is not placed on the plate $P_{30}$ (FIG. 4A), the front end SLT of the slope $SL_{30}$ is in a first position where the front end SLT is brought into contact with a floor F due to the weight of the slope $SL_{30}$. In that situation, since there is no height difference between the floor F and the slope $SL_{30}$, the caster CT easily moves obliquely upward along the upper surface (inclined surface) of the slope $SL_{30}$. Then, the caster CT reaches the front end of the plate $P_{30}$ of the main body 30M, namely, a position on the swing shaft $X_{30}$. So far, the guide 30G has no posture change.

Subsequently, when the caster CT that has reached the front end of the plate $P_{30}$ (i.e., the position on the swing shaft $X_{30}$) passes the position on the swing shaft $X_{30}$ and moves toward the short wall WS, the caster CT runs on a rectangular part RC of the lever $LV_{30}$ of the guide 30G which pushes the rectangular part RC downward. This causes the guide 30G to seesaw with the swing shaft $X_{30}$ as the center, fitting the lever $LV_{30}$ of the guide 30G in the recess $R_{30}$ of the plate $P_{30}$ of the main body 30M (FIG. 4B). The caster CT stops at the timing at which the caster CT comes into contact with the short wall WS, and the placement ends.

When the lever $LV_{30}$ is fitted into the recess $R_{30}$, the front end SLT of the slope $SL_{30}$ swings to be in a second position where the front end SLT is separated from the floor. In the second position, the entirety of the slope $SL_{30}$ including the front end SLT is separated from the floor. Further, a flat surface is defined by the upper surface of the plate $P_{30}$ and the upper surface of the lever $LV_{30}$ and the caster CT is positioned on the flat surface. This eliminates, for example, a measurement error which may otherwise be caused by movement of the caster CT due to the height difference between the upper surface of the plate $P_{30}$ and the upper surface of the rectangular part RC. In order to prevent rotational movement of the caster CT, the caster CT may be locked after being placed on the platform 30.

Figure 5:
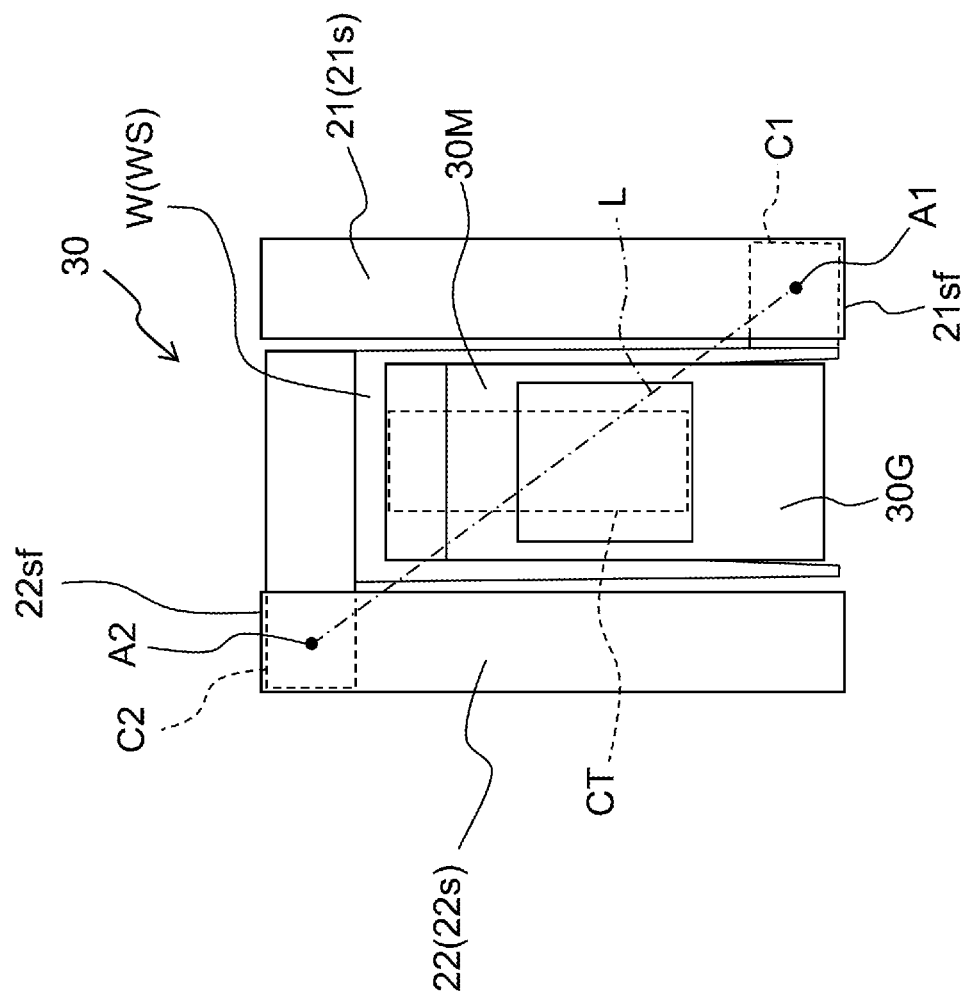
FIG. 5 is an illustrative view illustrating the relation between positions at which the platform is fixed to load cells and a proper placement position of an object to be detected (detection target) on the platform.

As depicted in FIG. 5, the platform 30 of the first embodiment is configured so that the center portion in plan view of the caster CT, which is brought into contact with the wall W and is placed on the plate $P_{30}$, is positioned, in plan view, on a line L or in the vicinity thereof. The line L connects a connection position between the first connection part C1 and the first load cell 21 and a connection position between the second connection part C2 and the second load cell 22. Although the line L is similar to the diagonal line of the plate $P_{30}$, they are not identical. The line L, however, may be identical to the diagonal line of the plate $P_{30}$.

Casters attached to other legs of the bed are similarly placed on pieces of the load detector 100.

The load of the human subject on the bed is transmitted to the flexure element $21s$ of the first load cell 21 and the flexure element $22s$ of the second load cell 22 that support the platform 30, via the bed leg BL, the caster CT, and the platform 30. The load transmitted generates the strain in the flexure element 21s and the flexure element 22s, and the strain gages 21g, 22g each detect the strain as the change in a resistance value. The change in the resistance value is outputted to the controller (not depicted in the drawing) that is provided outside the load detector 100, provided in the first base 11, or provided in the second base 12, via lead wires (not depicted in the drawing). Performing Arithmetic processing by the controller determines the load of the human subject.

Here, explanation is made about the reason why the load detector 100 of the first embodiment supports the platform 30 at two points by use of the first load cell 21 and the second load cell 22.

In the load detector 100 of the first embodiment, as depicted in FIG. 5, the main body 30M of the platform 30 is supported in the vicinity of the second end 21sf of the flexure element 21s of the first load cell 21 via the first connection part C1, and is supported in the vicinity of the second end 22sf of the flexure element 22s of the second load cell 22 via the second connection part C2, to be movable in the up-down direction.

Assuming that the center point of fixing of the first connection part C1 to the flexure element 21s is defined as a fixing center A1 and the center point of fixing of the second connection part C2 to the flexure element 22s is defined as a fixing center A2, the line L connecting the fixing center A1 and the fixing center A2 in the shortest distance is a part, of the main body 30M of the platform 30, which is least likely to bend. Thus, disposing the caster CT of the bed on the line L enables the detection of load of the human subject on the bed while reducing the effect of bending of the platform 30.

As described above, the main body 30M of the platform 30 of the load detector 100 according to the first embodiment is configured so that the caster CT brought into contact with the short wall WS is positioned on the line L or in the vicinity thereof. Thus, it is possible to detect a load of the human subject stably and precisely while disposing the caster CT on the line L or in the vicinity thereof in a stable fashion.

Figure 6:
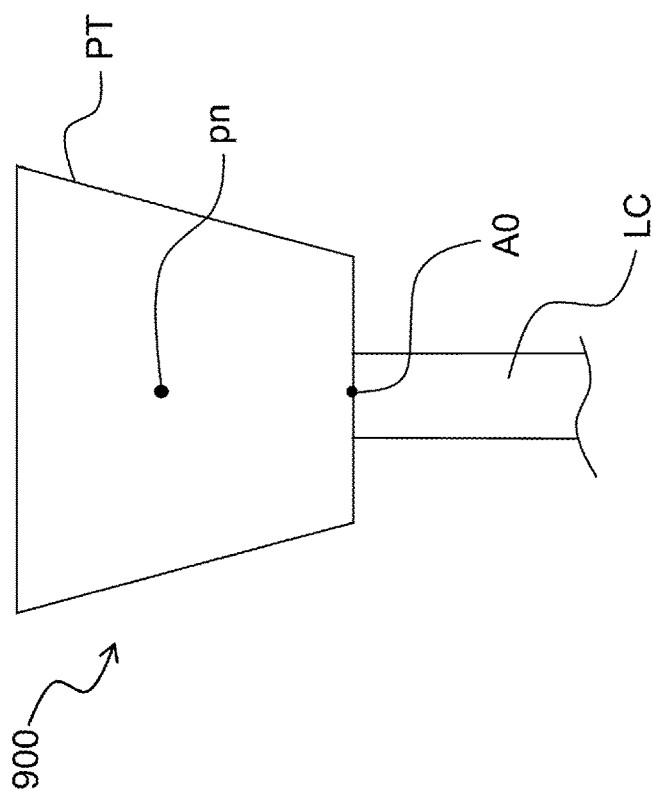
FIG. 6 is an illustrative view illustrating a placement position of a detection target on a mounting plate in a load detector using a single beam-type load cell.

When compared to a load detector (hereinafter referred to as a single-load-cell-type load detector) in which a mounting plate is attached to an end of a beam-type load cell, the load detector 100 of the present disclosure can detect a load more stably and accurately. The reason thereof is explained while referring to a single-load-cell-type load detector 900 depicted in FIG. 6. As depicted in FIG. 6, the single-load-cell-type load detector 900, in which a mounting plate PT is connected to an end of a beam-type load cell LC, has a relatively small position deviation error, in a case that a placement position pn of a detection target is in the vicinity of a connection position A0 between the beam-type load cell LC and the mounting plate PT. The position deviation error, however, increases as the distance between the placement position pn and the connection position A0 is longer. The reason thereof is as follows. Namely, as the distance between the placement position pn and the connection position A0 in the longitudinal direction of the beam-type load cell LC is longer, the bending moment, of which degree depends on the distance between the placement position pn and the connection position A0 in the longitudinal direction, acts on a flexure element of the beam-type load cell LC around an axis extending in the width direction of the beam-type load cell LC to cause the strain in the flexure element. This strain causes the position deviation error in a strain gage of the beam-type load cell LC. Further, as the distance between the placement position pn and the connection position A0 in the width direction of the beam-type load cell LC is longer, the torsional or twisting moment, of which degree depends on the distance between the placement position pn and the connection position A0 in the width direction, acts on the flexure element of the beam-type load cell LC around an axis extending in the longitudinal direction of the beam-type load cell LC to cause the strain in the flexure element. This strain causes the position deviation error in the strain gage of the beam-type load cell LC.

Figure 7:
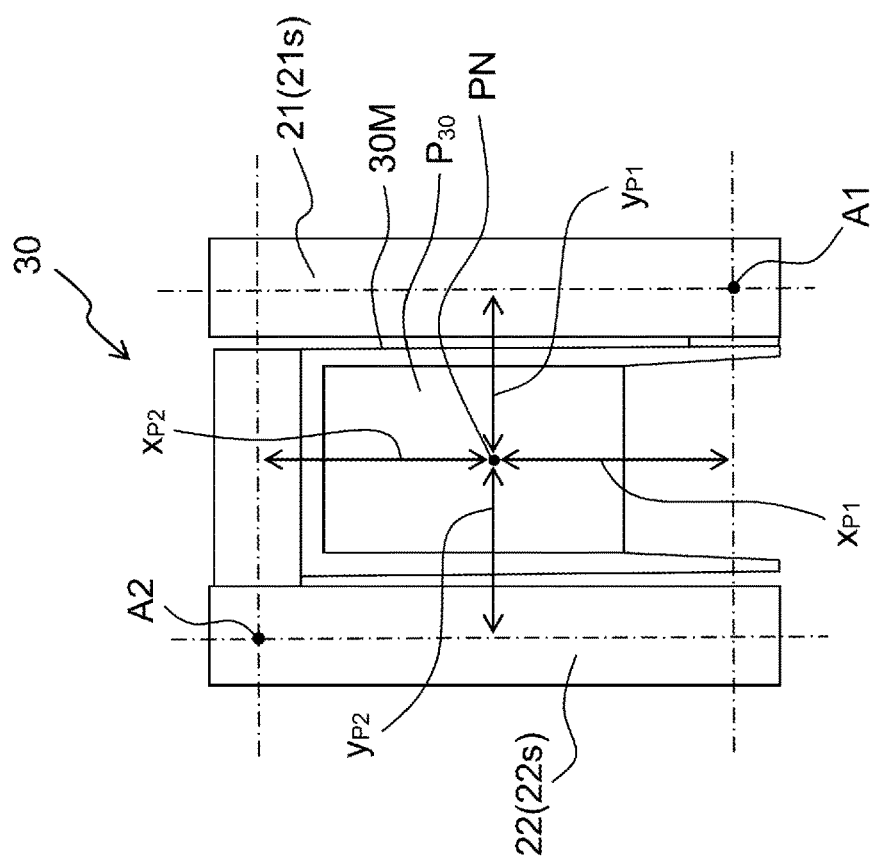
FIG. 7 is an illustrative view illustrating distances, in a longitudinal direction and a width direction, between a position of the detection target on the platform and positions at which the platform is fixed to the load cells.

In the load detector 100 of the first embodiment, as depicted in FIG. 7, assuming that a distance, in the longitudinal direction, between the fixing center A1 and a placement position PN of the detection target placed on the plate $P_{30}$ of the main body 30M of the platform 30 is defined as a distance $x_{P1}$ and that a distance, in the longitudinal direction, between the fixing center A2 and the placement position PN is defined as a distance $x_{P2}$, the total of the distances $x_{P1}$, $x_{P2}$ is constant over almost the whole area of the plate $P_{30}$ of the main body 30M. Thus, even when the placement position PN is displaced in the front-rear direction in the load detector 100 of the first embodiment, the total of the position deviation error caused in the first load cell 21 by the bending moment and the position deviation error caused in the second load cell 22 by the bending moment is approximately constant (a value having a certain ratio to the weight of the detection target) at all times. Therefore, the effect of the position deviation error caused by the bending moment is virtually removed, for example, by allowing the controller (not depicted in the drawings) to sum up detection values of the first load cell 21 and the second load cell 22 and to subtract a certain value (the value having the certain ratio to the weight of the detection target) as the position deviation error therefrom. Accordingly, the load of the detection target can be detected stably.

Further, as depicted in FIG. 7, assuming that a distance, in the width direction, between the fixing center A1 and the placement position PN of the detection target placed on the plate $P_{30}$ of the main body 30M is defined as a distance $y_{P1}$ and that a distance, in the width direction, between the fixing center A2 and the placement position PN is defined as a distance $y_{P2}$, the total of the distances $y_{P1}$, $y_{P2}$ is constant over almost the whole area of the plate $P_{30}$ of the main body 30M. Thus, even when the placement position PN is displaced in the width direction in the load detector 100 of the first embodiment, the total of the position deviation error caused in the first load cell 21 by the torsional moment and the position deviation error caused in the second load cell 22 by the torsional moment is approximately constant (a value having a certain ratio to the weight of the detection target) at all times. Therefore, the effect of the position deviation error caused by the torsional moment is virtually removed, for example, by allowing the controller (not depicted in the drawings) to sum up detection values of the first load cell 21 and the second load cell 22 and to subtract a certain value (the value having the certain ratio to the weight of the detection target) as the position deviation error therefrom. Accordingly, the load of the detection target can be detected stably.

Effects of the load detector 100 of the first embodiment are summarized as follows.

The platform 30 of the load detector 100 of the first embodiment includes the main body 30M and the guide 30G that is movable like a seesaw relative to the main body 30M. When the rolling body (e.g., the caster CT) as the detection target is introduced on the main body 30M, it is possible to use the slope $SL_{30}$ having the front end SLT brought into contact with the floor F. The detection target can thus be placed on the main body 30M easily.

In the platform 30 of the load detector 100 of the first embodiment, when the rolling body (e.g., the caster CT) as the detection target moves on the main body 30M, pushing the lever $LV_{30}$ of the guide 30G toward the main body 30M causes the guide 30G to move like a seesaw (swing), which separates the front end SLT of the slope $SL_{30}$ from the floor F. The state where the slope $SL_{30}$ is separated from the floor F is maintained as long as the rolling body is present on the main body 30M. Thus, the load detection that is performed by placing the detection target on the main body 30M does not have a measurement error which may otherwise be caused by the contact between the guide 30G and the floor F.

In the platform 30 of the load detector 100 of the first embodiment, most of the load from the rolling body (e.g., the caster CT) is applied to the plate $P_{30}$, and only a part of the load from the rolling body (e.g., the caster CT) is applied to the guide 30G via the rectangular part RC of the lever $LV_{30}$. That configuration reduces the load applied to the swing shaft $X_{30}$ over time, preventing components or parts, such as the bosses B and the recessed holes C, from being damaged. It is desired that the depth of the recess $R_{30}$ (the height of the upper surface of the plate $P_{30}$ relative to the bottom surface of the recess $R_{30}$) is greater than the thickness of the lever $LV_{30}$. This configuration has a gap (backlash) between the lower surface of the lever $LV_{30}$ and the bottom surface of the recess $R_{30}$, and the load from the rolling body (e.g., the caster CT) is applied only to the plate $P_{30}$, making it possible to further reduce the load on the swing shaft $X_{30}$.

In the load detector 100 of the first embodiment, the platform 30 includes the first connection part C1 and the second connection part C2 on both sides in the diagonal direction of the plate $P_{30}$ of the main body 30M, and the platform 30 is supported by the first load cell 21 and the second load cell 22 via the first connection part C1 and the second connection part C2 to be movable in the up-down direction. In that configuration, disposing the detection target on the line L (that is similar to or the same as the diagonal line of the plate $P_{30}$) connecting the connection position between the first connection part C1 and the first load cell 21 and the connection position between the second connection part C2 and the second load cell 22 results in a successful load detection of the detection target without suffering the effect of bending of the plate $P_{30}$.

In the load detector 100 of the first embodiment, the total value of position deviation errors that are caused in the first and second load cells 21, 22 by the bending moment and the total value of position deviation errors that are caused in the first and second load cells 21, 22 by the torsional moment are approximately constant at all times. Therefore, the effect of each position deviation error is virtually removed by summing up detection values of the first load cell 21 and the second load cell 22 and subtracting the position deviation error, which is an approximately constant value, therefrom. Accordingly, the load detection can be performed stably and precisely.

In the load detector 100 of the first embodiment, the first arm AM1 and the second arm AM2 of the lever $LV_{30}$ of the guide 30G of the platform 30 may be connected to the slope $SL_{30}$ in the vicinity of the center portion in the longitudinal direction of the slope $SL_{30}$. Any one of the first arm AM1 and the second arm AM2 may be omitted. The number of arms and the arrangement thereof may be changed so that the rolling body placed on the platform 30 does not apply an unnecessary load to the guide 30G via the arm(s).

First Modified Example

Figure 8:
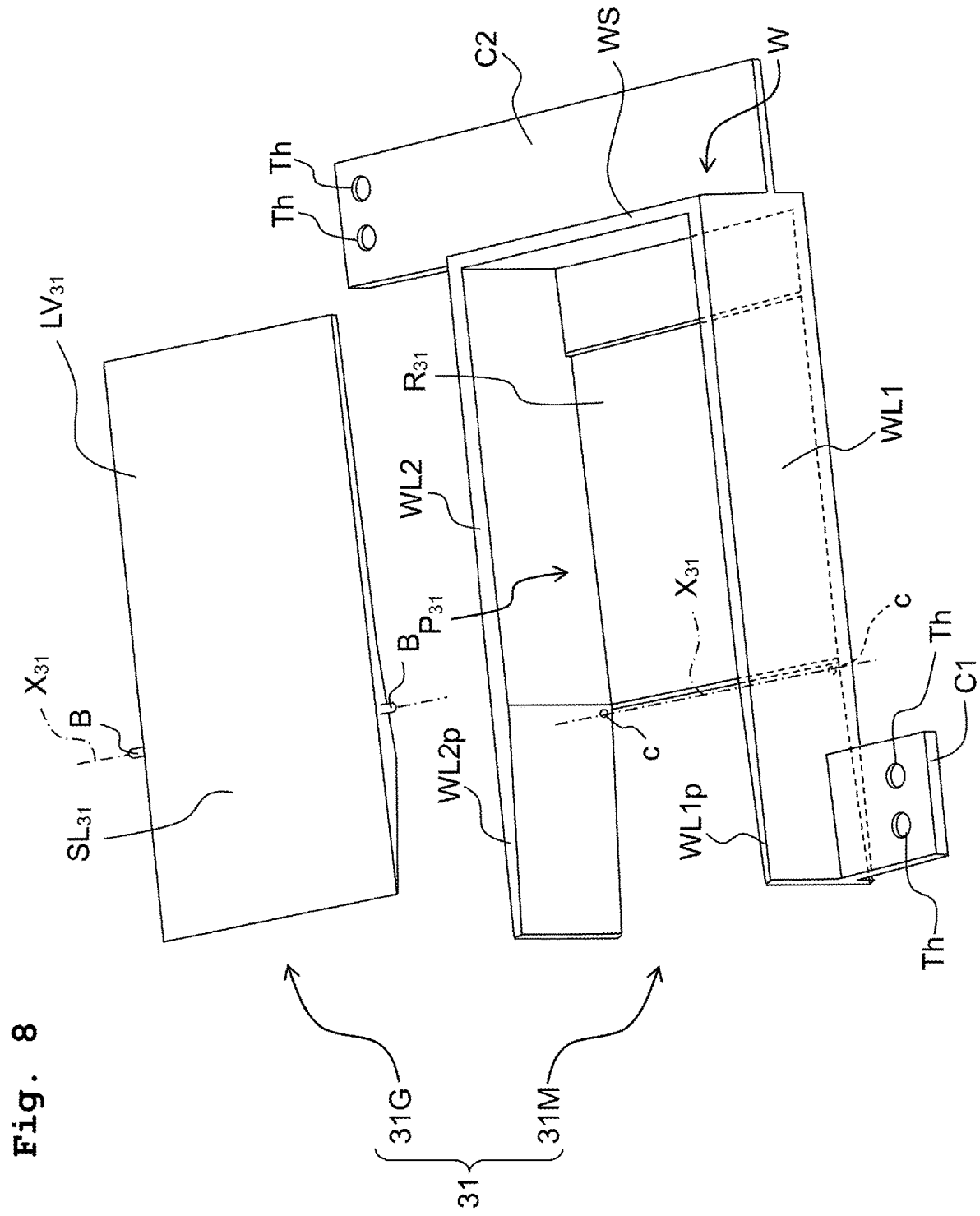
FIG. 8 is an exploded perspective view of a platform according to a first modified example of the present disclosure.
Figure 9:
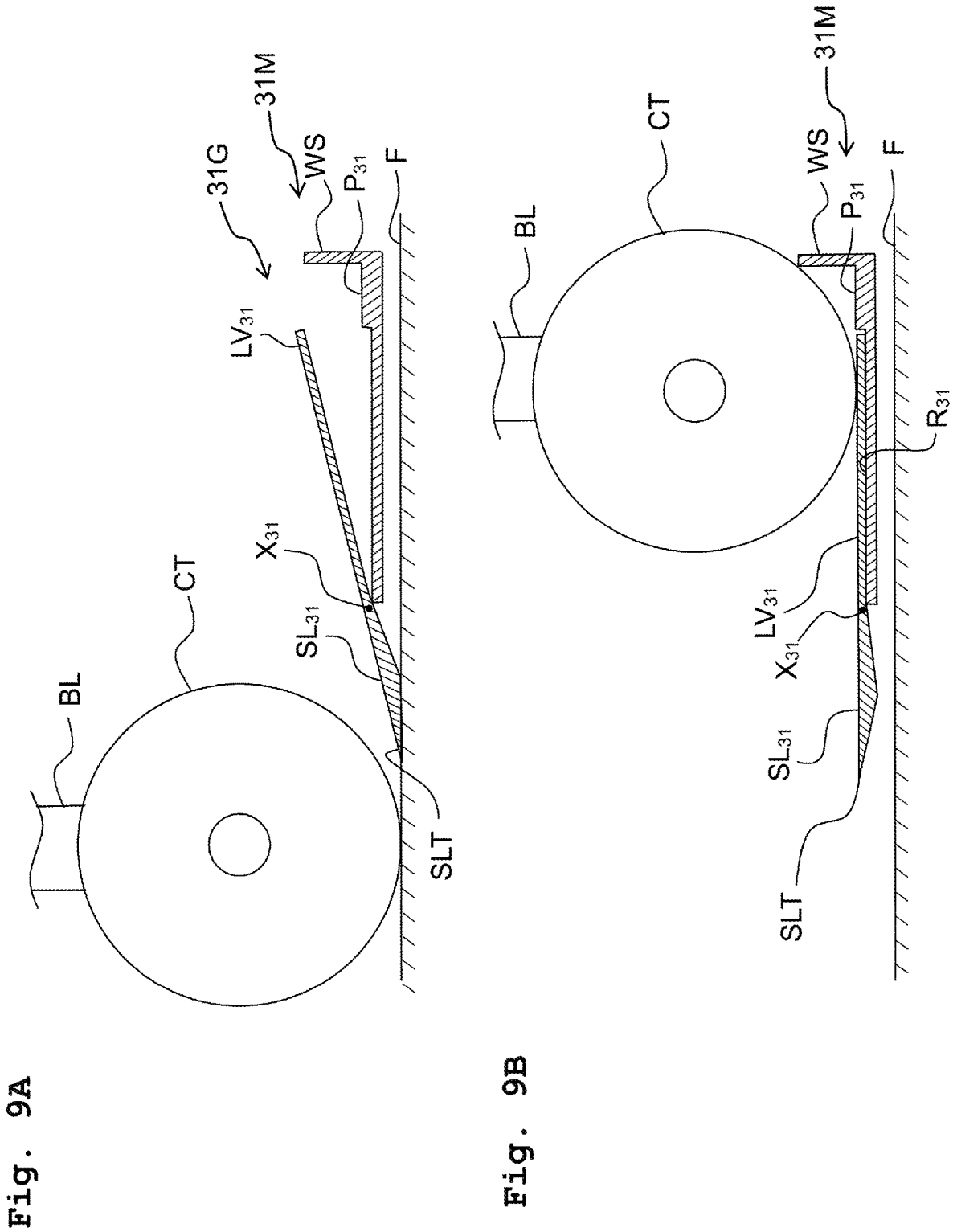
FIG. 9A depicts placement of the caster on the platform according to the first modified example of the present disclosure, in particular, a situation before the caster is placed on the platform.
FIG. 9B depicts placement of the caster on the platform according to the first modified example of the present disclosure, in particular, a situation after the caster is placed on the platform.

Referring to FIGS. 8, 9A, and 9B, explanation is made about a platform of the load detector 100 according to a first modified example. A platform 31 of the first modified example is the same as the platform 30 of the first embodiment, except that a lever $LV_{31}$ of a guide 31G is a rectangular flat plate having no opening, that a recess $R_{31}$ having a rectangular shape in plan view is provided in a plate $P_{31}$ of a main body 31M instead of the recess $R_{30}$ having substantially a C-shape in plan view, and that the guide 31G is connected to the main body 31M by fitting the bosses B provided in the slope $SL_{31}$ into the recess holes c provided in the wall W of the main body 31M.

As depicted in FIGS. 9A and 9B, the rolling body (e.g., the caster CT) can be introduced on the platform 31 of the first modified example, similarly to the introduction of the rolling body on the platform 30 provided in the load detector 100 of the first embodiment. In the first modified example, the caster CT that passed a position on a swing shaft $X_{31}$ runs on the lever $LV_{31}$ of the guide 31G, pushing the lever $LV_{31}$ downward. This causes the guide 31G to move like a seesaw around the swing shaft $X_{31}$, the lever $LV_{31}$ of the guide 31G is fitted into the recess $R_{31}$ of the plate $P_{31}$ of the main body 31M, and thus the entirety of the slope $SL_{31}$ including the front end SLT is separated from the floor. The caster CT stops at the timing at which the caster CT comes into contact with the short wall WS, and the placement ends.

In the platform 31 of the first modified example, the caster CT that passes the position on the swing shaft $X_{31}$ and runs toward the short wall WS moves rotatably only on the upper surface of the lever $LV_{31}$ having a flat plate shape, and then placed on the upper surface of the lever $LV_{31}$. The lever $LV_{31}$ is flat, has no opening, and has no height difference between the lever $LV_{31}$ and another part. In that configuration, the caster CT is surely placed on the flat surface irrespective of the position on the platform where the caster CT stops. This prevents a measurement error which may otherwise be caused by the height difference, between the lever $LV_{31}$ and another part, which would affect the caster CT.

Second Embodiment

Figure 10:
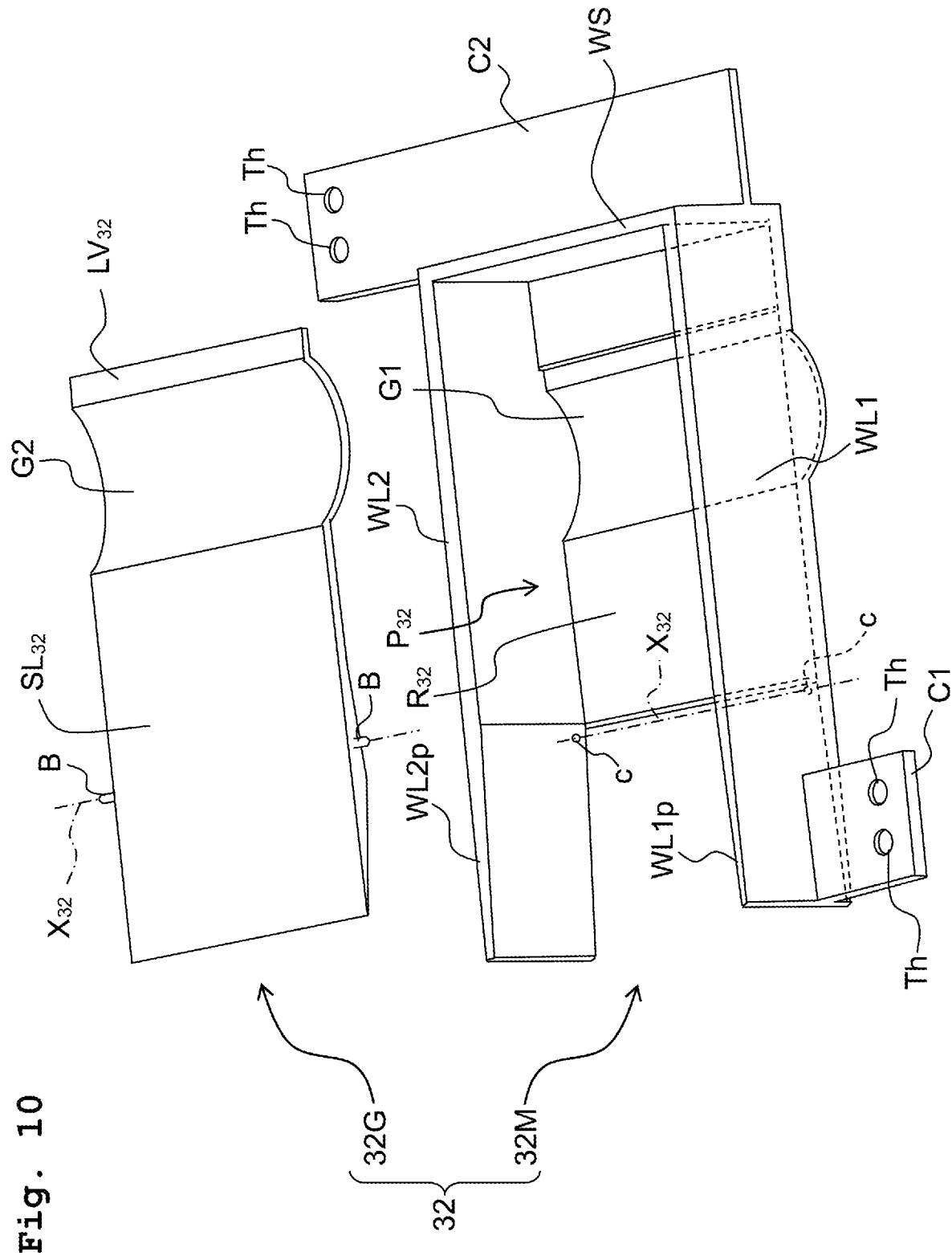
FIG. 10 is an exploded perspective view of a platform according to a second embodiment of the present disclosure.

Referring to FIGS. 10, 11A, and 11B, a platform of the load detector 100 according to a second embodiment is explained. A platform 32 of the second embodiment is the same as the platform 31 of the first modified example, except that a groove G1 having an arc-like shape and extending in the short-side direction of a plate $P_{32}$ is provided in a recess $R_{32}$, which has a rectangular shape in plan view, of the plate $P_{32}$ of a main body 32M, and that a groove (movement regulation part) G2 which has an arc-like shape and of which shape and arrangement correspond to those of the groove G1, is provided in a lever $LV_{32}$ of a guide 32G As depicted in FIGS. 11A and 11B, the rolling body (e.g., the caster CT) can be introduced on the platform 32 of the second embodiment, similarly to the introduction of the rolling body on the platform 31 of the first modified example. In the second embodiment, the caster CT that passed a position on a swing shaft $X_{32}$ runs on the lever $LV_{32}$ of the guide 32Q pushing the lever $LV_{32}$ downward. This causes the guide 32G to move like a seesaw around the swing shaft $X_{32}$, fitting the lever $LV_{32}$ of the guide 32G into the recess $R_{32}$ of the plate $P_{32}$ of the main body 32M and fitting the groove G2 of the lever $LV_{32}$ into the groove G1 of the recess $R_{32}$. In that situation, the entirety of the slope $SL_{32}$ including the front end SLT is separated from the floor. The caster CT that passes the position on the swing shaft $X_{32}$ and moves toward the short wall WS runs on the lever $LV_{32}$, and stops by being fitted into the groove G2 (FIG. 11B). Namely, the groove G2 functions to position the caster CT at an appropriate detection position on the platform 32. The groove G2 also functions to keep the caster CT on the platform 32 even when force acts on the caster CT due to an earthquake, an unexpected contact, or an unexpected collision. The shapes of the grooves G1 and G2 are not limited to those depicted in FIGS. 11A and 11B, and each of the grooves G1 and G2 may have any shape.

Second Modified Example

Figure 12:
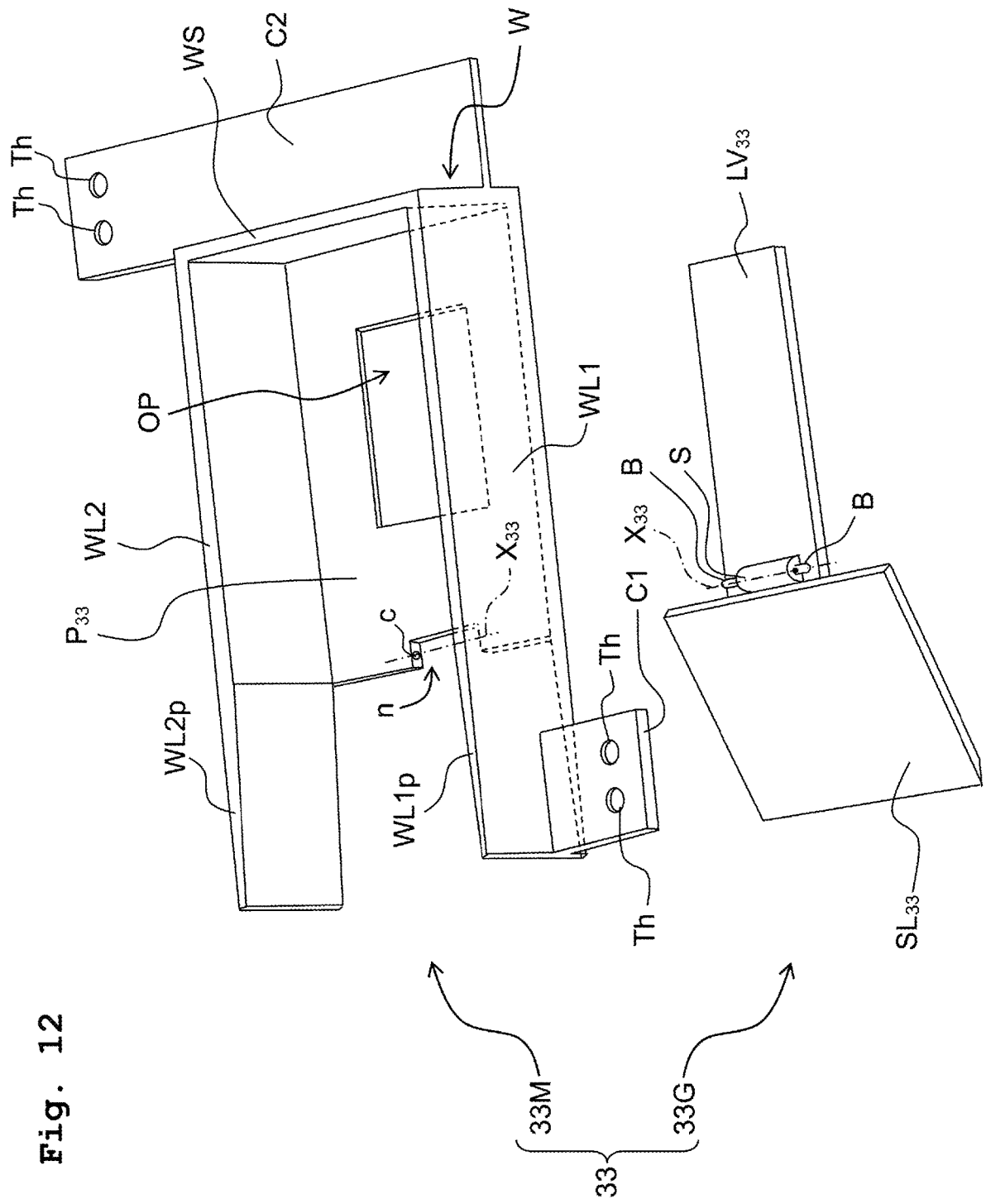
FIG. 12 is an exploded perspective view of a platform according to a second modified example of the present disclosure.

Referring to FIGS. 12, 13A, and 13B, explanation is made about a second modified example of the platform 30 of the load detector 100 according to the first embodiment. A platform 33 of the second modified example is mainly different from the platform 30 of the load detector 100 according to the first embodiment in that a lever $LV_{33}$ of a guide 33G is a member that is rectangular in plan view and is disposed below a main body 33M, and that a plate $P_{33}$ of the main body 33M is a flat plate having an opening OP. The guide 33G is attached to the main body 33M so that the guide 33G moves like a seesaw around a swing shaft $X_{33}$ by fitting the bosses B protruding from the shaft support part S of the lever $LV_{33}$ into the recessed holes c of the notch n of the plate $P_{33}$ of the main body 33M. In that situation, the lever $LV_{33}$ is disposed below the opening OP.

As depicted in FIGS. 13A and 13B, the rolling body (e.g., the caster CT) can be introduced on the platform 33 of the second modified example, similarly to the introduction of the rolling body on the platform 30 of the load detector 100 of the first embodiment. In the second modified example, the caster CT that passed a position on the swing shaft $X_{33}$ runs on the plate $P_{33}$ of the main body 33M toward the short wall WS. Then, the caster CT stops by being fitted into the opening OP of the plate $P_{33}$, which pushes the lever $LV_{33}$ of the guide 33G downward. This causes the guide 33G to move like a seesaw around the swing shaft $X_{33}$, and the entirety of a slope $SL_{33}$ including the front end SLT is separated from the floor F.

Similar to the groove G2 of the second embodiment, the opening OP of the plate $P_{33}$ of the second modified example positions the caster CT at an appropriate detection position and prevents the caster CT from falling from the platform 33 due to unexpected external force. Further, in the second modified example, fitting the rolling body (e.g., the caster CT) into the opening OP causes the guide 33G to swing, which moves the slope $SL_{33}$ upward. In that configuration, a user can check whether the rolling body (e.g., the caster CT) is fitted into the opening OP and positioned at the appropriate detection position only by visually checking, at the time of placement for example, whether the front end SLT of the slope $SL_{33}$ moves upward.

In the platform 33 of the second modified example, the entire load of the caster CT is applied to the main body 33M in the state where the caster CT is fitted into the opening OP and positioned at the appropriate detection position. That configuration reduces the load applied to the swing shaft $X_{33}$ over time, preventing components or parts, such as the bosses B and the recessed holes C, from being damaged.

Third Modified Example

Figure 14:
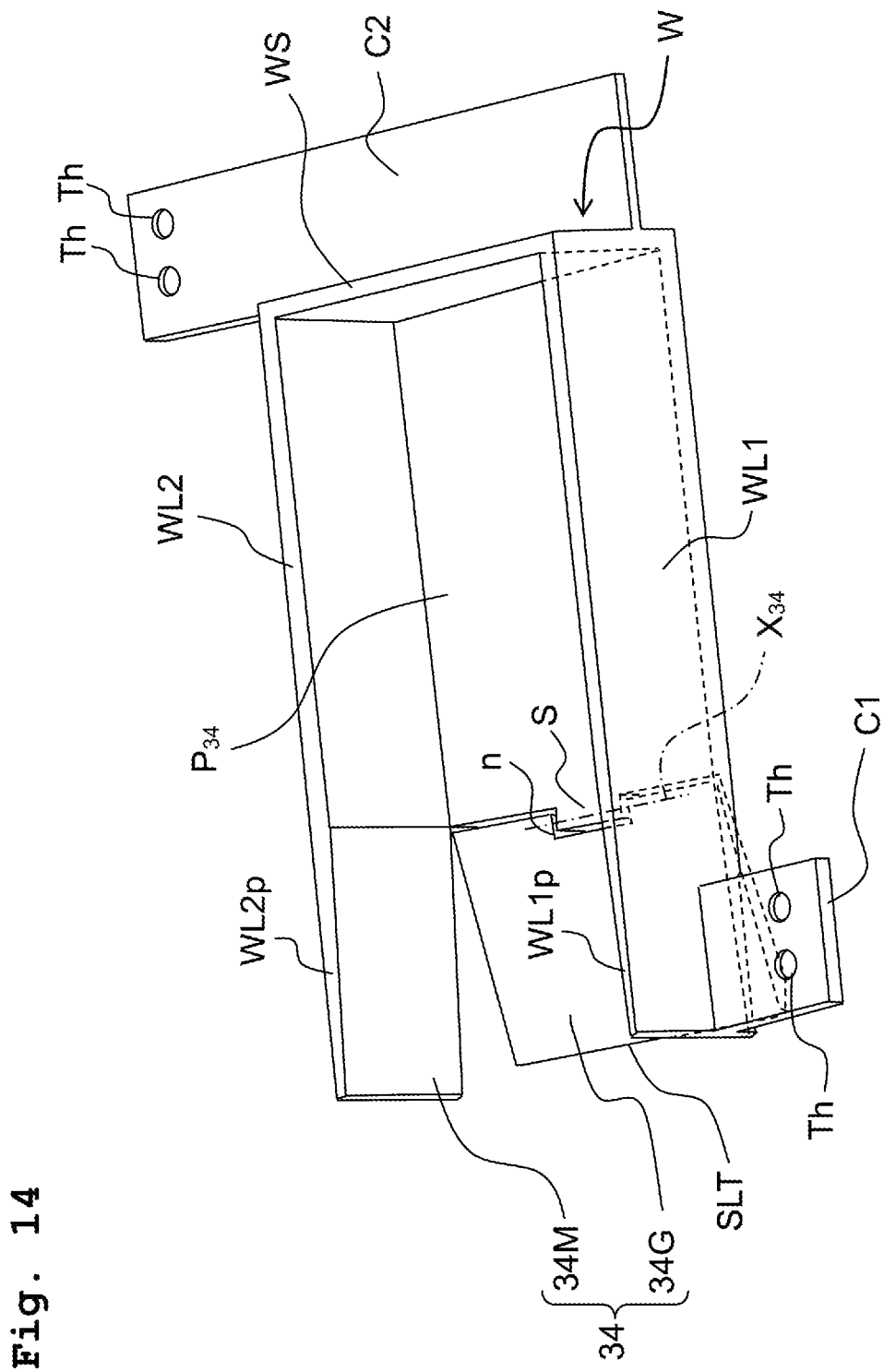
FIG. 14 is a perspective view of a platform according to a third modified example of the present disclosure.

Referring to FIGS. 14, 15A, and 15B, explanation is made about a second modified example of the platform 30 of the load detector 100 of the first embodiment. A platform 34 of the third modified example is the same as the platform 30 of the load detector 100 of the first embodiment, except that a guide 34G has no lever, no recess is formed on the upper surface of a plate $P_{34}$ of a main body 34M, and an urging (biasing) member that urges (biases) the front end SLT of the guide 34G upward is provided. Specifically, the urging member is torsion spring(s) (not depicted) that is/are disposed to surround boss(es) (not depicted) protruding from the shaft support part S.

In the platform 34 of the third modified example, the front end SLT of the guide 34G is in the second position where the front end SLT is separated from the floor F, even when the rolling body (e.g., the caster CT) is not placed on the platform 34. The front end SLT is in the first position where the front end SLT is brought into contact with the floor F, only when the rolling body is positioned on the guide 34G. In that point, the platform 34 is different from the platforms 30, 31, 32, and 33 according to the above embodiments and modified examples in which the front end SLT of the slope is in the first position where the front end SLT is brought into contact with the floor F when the rolling body is not placed on each of the platforms 30, 31, 32, and 33.

When the caster CT is introduced on the platform 34, the caster CT may be positioned on the floor F in the vicinity of the platform 34 (FIG. 15A). In that case, the guide 34G of the platform 34 is urged by the torsion spring(s), so that the front end SLT of the guide 34G is in the second position where the front end SLT is separated from the floor F.

Subsequently, when the caster CT approaches the platform 34, the caster CT runs on the front end SLT of the guide 34G and pushes the guide 34G downward. This causes the guide 34G to move like a seesaw (to swing) around a swing shaft $X_{34}$, making the front end SLT contact with the floor F (FIG. 15B). Accordingly, the caster CT runs on a slope defined on the upper surface of the guide 34G rotatably moves obliquely upward on the slope, and reaches the main body 34M.

In a state where the caster CT is placed on the plate $P_{34}$ of the main body 34M, no pushing force acting downward is applied to the guide 34G. In that case, the front end SLT of the guide 34G is urged by the torsion spring(s), keeping the front end SLT in the second position where the front end SLT is separated from the floor F.

In the platform 34 of the third modified example, the rolling body that passes a position on the swing shaft $X_{34}$ and moves toward the short wall WS rotatably moves only on the upper surface of the flat plate $P_{34}$ of the main body 34M and then is placed on the upper surface of the plate $P_{34}$. This prevents a measurement error which may otherwise be caused by the height difference, between the upper surface of the plate $P_{34}$ and another part, which would affect the caster CT.

The platform 34 of the third modified example may not have a structure that urges the front end SLT of the guide 34G upward, such as the torsion spring. In that configuration, for example, the guide 34G is attached to the main body 34M in accordance with such an aspect that the upper surface of the guide 34G can swingably move to a position where the upper surface of the guide 34G comes into contact with the upper surface of the plate $P_{34}$. When using the load detector, a user manually operates the guide 34G so that the guide 34G swings. After the user places the rolling body (e.g., the caster CT) on the platform 34, the guide 34G is kept on the plate $P_{34}$ in a state where the upper surface of the guide 34G is brought into contact with the upper surface of the plate $P_{34}$.

The following modifications can be applied to the first and second embodiments and the first to third modified examples.

Figure 16:
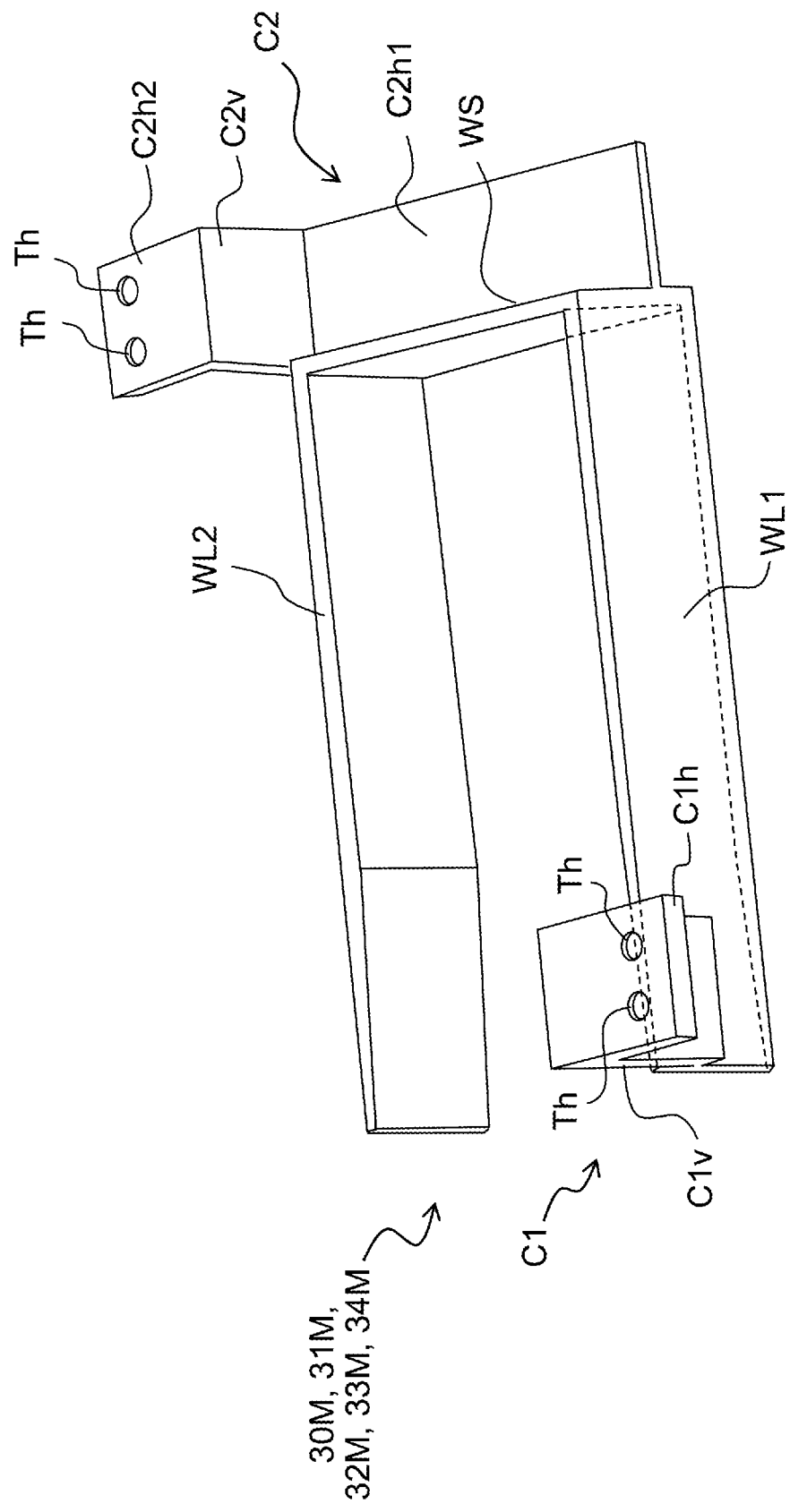
FIG. 16 is a modified aspect of a first connection part and a second connection part of the platforms according to the embodiments and the modified examples, wherein only a wall of a main body, of which shape is common in the embodiments and the modified examples, is depicted and the illustration of a plate is omitted.

The first connection part C1 and the second connection part C2 included in the main bodies 30M, 31M, 32M, 33M, and 34M of the platforms 30, 31, 32, 33, and 34 according to the embodiments and the modified examples may be configured as depicted in FIG. 16. Namely, the first connection part C1 has a vertical part C1$v$ extending upward and parallel to the first long wall WL1, and a horizonal part C1$h$ extending from the upper end of the vertical part C1$v$ in the horizonal direction, which is perpendicular (orthogonal) to the vertical part C1$v$. The second connection part C2 has a first horizonal part C2$h$1 having a rectangular shape in plan view and extending from the short wall WS in the horizontal direction, a vertical part C2$v$ extending upward from a short side on the second long wall WL2 side of the first horizontal part C2$h$1, and a second horizonal part C2$h$2 extending from the upper end of the vertical part C2$v$ in the horizonal direction, which is perpendicular to the vertical part C2$v$. The first connection part C1 is connected to the upper surface 21$st$ of the flexure element 21$s$ in the vicinity of the second end 21$sf$ of the flexure element 21$s$ of the first load cell 21. The second connection part C2 is connected to the upper surface 22$st$ of the flexure element 22$s$ in the vicinity of the second end 22$sf$ of the flexure element 22$s$ of the second load cell 22.

In the platforms 30, 31, 32, 33 and 34 of the above embodiments and modified examples, the first connection part C1 may be a surface connected to the front end of the protrusion WL1$p$ of the first long wall WL1 and parallel to the short wall WS. In that case, the platform is attached to the first load cell 21 by fixing the surface to an end surface in the longitudinal direction of the flexure element 21$s$ of the first load cell 21. The same is true of the second connection part C2.

In each of the platforms 30, 31, 32, 33, and 34 of the above embodiments and modified examples, it is not indispensable to arrange the first connection part C1 and the second connection part C2 on the diagonal line of each of the plates $P_{30}$, $P_{31}$, $P_{32}$, $P_{33}$, and $P_{34}$ provided that the first connection part C1 and the second connection part C2 are arranged with each of the plates $P_{30}$, $P_{31}$, $P_{32}$, $P_{33}$, and $P_{34}$ intervening therebetween in the diagonal direction.

It is not indispensable to attach the first connection part C1 of each of the platforms 30, 31, 32, 33, and 34 of the above embodiments and modified examples to the vicinity of the second end 21$sf$ of the flexure element 21$s$ of the first load cell 21. The first connection part C1 may be attached to the flexure element 21$s$ of the first load cell 21 on the second end 21$sf$ side (free end side) relative to the center portion in the longitudinal direction. The first connection part C1 may be attached to the flexure element 21$s$ of the first load cell 21 at any position on the free end side of the thin part 21$th$. The same is true of the attachment of the second connection part C2 to the flexure element 22$s$ of the second load cell 22. The second connection part C2 may be attached to the flexure element 22$s$ of the second load cell 22 on the second end 22$sf$ side (free end side) relative to the center portion in the longitudinal direction.

Each of the platforms 30, 31, 32, 33, and 34 of the above embodiments and modified examples can be used as a platform of the single-load-cell-type load detector 900 such as depicted in FIG. 6. In that case, for example, the first connection part C1 and the second connection part C2 are not required to be provided in the main bodies 30M, 31M, 32M, 33M, and 34M of the platforms 30, 31, 32, 33, and 34. The front end of the load cell LC is fixed and connected to the short wall WS. Further, each of the platforms 30, 31, 32, 33, and 34 of the above embodiments and modified examples can be used as a measuring pan of a load scale having three load cell sensors, such as described in Patent Literature 1.

Each of the platforms 30, 31, 32, 33, and 34 of the above embodiments and modified examples may not have the wall W.

In each of the platforms 30, 31, 32, 33, and 34 of the above embodiments and modified examples, the above-described method of connecting each of the guides 30G 31G 32G 33G and 34G to the corresponding one of the main bodies 30M, 31M, 32M, 33M, and 34M in such a manner that the guide can move like a seesaw or can swing relative to the main body is an example, and any other method may be used. For example, the positional relation between the bosses B and the recessed parts c used in the platform 30 of the first embodiment may be opposite thereto. A shaft may pass through the guide instead of providing the bosses B.

In the platforms 30, 31, 32, and 33 according to the first embodiment, the first modified example, the second embodiment, and the second modified example, the slopes $SL_{30}$, $SL_{31}$, $SL_{32}$, and $SL_{33}$ of the guides 30G 31G 32G and 33G move to the positions in contact with the floor F, due to their own weight. The present disclosure, however, is not limited thereto. An urging member (e.g., a torsion spring, a plate spring, and a magnet) that urges the front end SLT of each of the slopes $SL_{30}$, $SL_{31}$, $SL_{32}$, and $SL_{33}$ downward may be provided between each of the main bodies 30M, 31M, 32M, and 33M and each of the guides 30G 31G 32G and 33G of each of the platforms 30, 31, 32, and 33. Or, a weight may be attached to each of the slopes $SL_{30}$, $SL_{31}$, $SL_{32}$, and $SL_{33}$ of the corresponding one of guides 30G 31G 32G and 33G thus moving the front end SLT of each of the slopes $SL_{30}$, $SL_{31}$, $SL_{32}$, and $SL_{33}$ downward.

In the load detector 100, the first base 11 and the second base 12 are parts or components separated from each other. The present disclosure, however, is not limited thereto. The first base 11 and the second base 12 may be formed integrally. For example, a flat plate extending below each of the platforms 30, 31, 32, 33, and 34 may connect the flat plate 11$a$ and the flat plate 12$a$.

In the load detector 100, the first load cell 21 and the second load cell 22 face each other in parallel. The first load cell 21 and the second load cell 22, however, may face each other while having an angle smaller than about 5°.

In the load detector 100, two strain gages 21$g$ are attached to the flexure element 21$s$ of the first load cell 21 and two strain gages 22$g$ are attached to the flexure element 22$s$ of the second load cell 22. The present disclosure, however, is not limited thereto, and three or more of strain gages 21$g$, 22$g$ may be attached to the flexure elements 21$s$, 22$s$, respectively.

Third Embodiment

Figure 17:
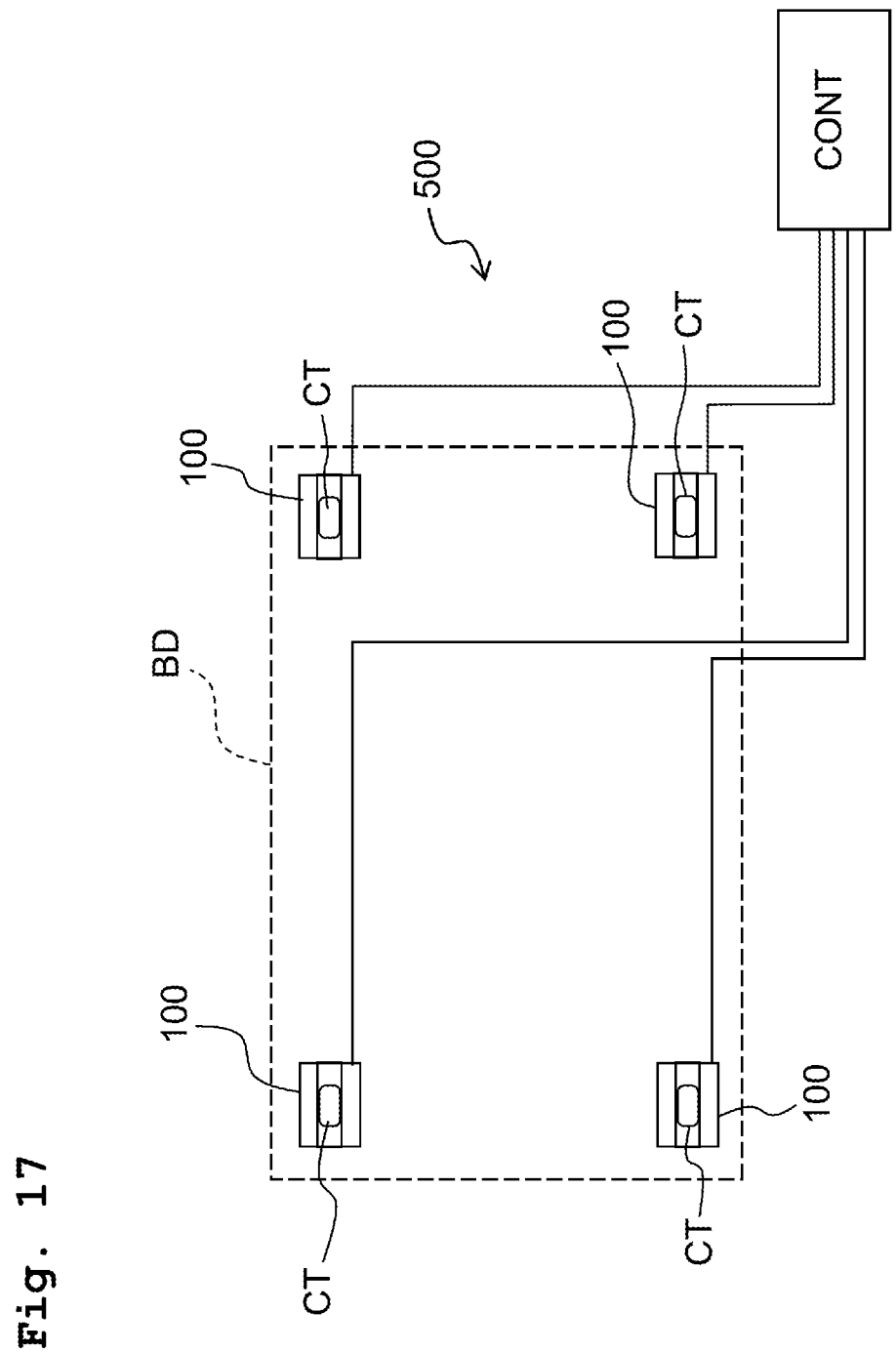
FIG. 17 is a schematic view depicting a configuration of a load detection system according to a third embodiment of the present disclosure.

Referring to FIG. 17, explanation is made about a load detection system 500 according to a third embodiment.

The load detection system 500 mainly includes four load detectors 100 and a controller CONT. The four load detectors 100 are connected to the controller CONT by wiring.

When the load detection system 500 is used, four casters CT fixed one-to-one to four legs of a bed BD are respectively placed on the platforms 30 of the four load detectors 100 (FIG. 4B). This allows each of the four load detectors 100 to detect a part of the load, of a human subject on the bed BD, which is applied to each detector via the corresponding leg of the bed BD.

The controller CONT connected to the four load detectors 100 executes load calculation processing in which the output from the first load cell 21 and the output from the second load cell 22 of each load detector 100 are summed and a certain value corresponding to a position deviation error is subtracted, and load summing-up processing in which the loads detected by the load detectors 100 are summed. The controller CONT may execute any other processing.

The load detection system of the third embodiment uses the load detector 100 including the platform 30 according to the first embodiment, thereby obtaining the same effects as those of the platform 30 according to the first embodiment. Specifically, the bed BD can be placed on the four platforms 30 only by moving the bed BD in one direction so that the four casters CT of the bed BD rotate to run on the slope $SL_{30}$ of the guide 30M. This achieves the placement of the bed BD on the load detectors 100 with less trouble and less manpower.

In the load detection system of the third embodiment, the number of load detectors 100 is not limited to four. Three or less or five or more of load detectors 100 may be used in the load detection system. Further, the load detector 100 may include, instead of the platform 30, each of the platform 31, 32, 33, and 34 according to the second embodiment and the modified examples.

In the load detection system of the third embodiment, the output from each load detector 100 may be transmitted to the controller CONT wirelessly rather than wiring. The controller CONT may be connected to an indicator indicating the load determined by the controller CONT and an alarm giving a predefined alarm based on the determined load.

The present invention is not limited to the above embodiments and its modified examples provided that the characteristics of the present invention can be obtained. The present invention includes any other embodiments which can be conceived in the range of the technical ideas of the present invention.

The load detector according to the above embodiments may further include a lever connected to the first end of the slope and extending from the first end of the slope toward an opposite side of the second end of the slope.

In the load detector according to the above embodiments, the lever may include a contact part configured to move by being pushed by the subject on the main body and an arm connecting the contact part and the slope.

In the load detector according to the above embodiments, a recess configured to accommodate the lever may be provided in an upper surface of the main body.

In the load detector according to the above embodiments, the lever may include a movement regulation part configured to regulate movement of the subject placed on the main body.

In the load detector according to the above embodiments, the main body may include an opening. The load detector according to the above embodiments may further include a lever connected to the first end of the slope and disposed below the main body to cover the opening.

The load detector according to the above embodiments may further include an urging member configured to urge the second end of the slope toward the second position.

In the load detector according to the above embodiments, the main body may include a plate configured to keep or retain the subject during load detection and a wall provided on the plate.

In the load detector according to the above embodiments, the beam-type load cell may include a first beam-type load cell which is supported on a first support base in a cantilever manner to have a free end and a second beam-type load cell which is disposed to face the first beam-type load cell and which is supported on a second support base in a cantilever manner to have a free end. The platform may be provided between the first beam-type load cell and the second beam-type load cell and may further include a first connection part connected to the first beam-type load cell and a second connection part connected to the second beam-type load cell. The free end of the first beam-type load cell and the free end of the second beam-type load cell may face opposite directions to each other in an extending direction of the first beam-type load cell. The first connection part of the platform may be connected to the first beam-type load cell on a side of the free end of the first beam-type load cell and the second connection part of the platform may be connected to the second beam-type load cell on a side of the free end of the second beam-type load cell.

In the load detector according to the above embodiments, the first beam-type load cell may be disposed parallel to the second beam-type load cell.

The load detector of one aspect of the present disclosure allows a detection target to be easily placed thereon and is capable of preventing or reducing a measurement error.

The load detector and the load detection system according to an aspect of the present disclosure are capable of easily placing a rolling body (e.g., a caster) on a platform through a slope and detecting a load while preventing an error which may otherwise be caused by the slope. Thus, when the load detector and the load detection system according to an aspect of the present disclosure are used in hospitals, nursing homes, and the like, the load detector can be easily disposed under a bed or the like with less manpower, thereby contributing to improvement of medical treatment quality, nursing quality, and the like.

Further, the present invention can be described in accordance with the following items:

1. A load detector, comprising:
   a beam-type load cell which is supported on a support base in a cantilever manner; and
   a platform connected to the beam-type load cell,
   wherein the platform includes a main body on which a subject is to be placed and a slope having a first end, which is connected to the main body, the slope being configured to guide the subject to the main body, and
   the slope is configured to swing between a first position in which a second end of the slope is in contact with a placement surface on which the load detector is placed and a second position in which the second end is separated from the placement surface.

2. The load detector according to item 1, further comprising a lever connected to the first end of the slope and extending from the first end of the slope toward an opposite side of the second end of the slope.

3. The load detector according to item 2, wherein the lever includes a contact part configured to move by being pushed by the subject on the main body and an arm connecting the contact part and the slope.

4. The load detector according to item 2 or 3, wherein a recess configured to accommodate the lever is provided in an upper surface of the main body.

5. The load detector according to any one of items 2 to 4, wherein the lever includes a movement regulation part configured to regulate movement of the subject placed on the main body.

6. The load detector according to item 1, wherein the main body includes an opening and
the load detector further includes a lever connected to the first end of the slope and disposed below the main body to cover the opening.

7. The load detector according to item 1, further comprising an urging member configured to urge the second end of the slope toward the second position.

8. The load detector according to any one of items 1 to 7, wherein the main body includes a plate configured to keep or retain the subject during load detection and a wall provided on the plate.

9. The load detector according to any one of items 1 to 8,
wherein the beam-type load cell includes a first beam-type load cell which is supported on a first support base in a cantilever manner to have a free end and a second beam-type load cell which is disposed to face the first beam-type load cell and which is supported on a second support base in a cantilever manner to have a free end,
the platform is provided between the first beam-type load cell and the second beam-type load cell and further includes a first connection part connected to the first beam-type load cell and a second connection part connected to the second beam-type load cell,
the free end of the first beam-type load cell and the free end of the second beam-type load cell face opposite directions to each other in an extending direction of the first beam-type load cell, and
the first connection part of the platform is connected to the first beam-type load cell on a side of the free end of the first beam-type load cell and the second connection part of the platform is connected to the second beam-type load cell on a side of the free end of the second beam-type load cell.

10. The load detector according to item 9, wherein the first beam-type load cell is disposed parallel to the second beam-type load cell.

11. A load detection system configured to detect a load of a human subject on a bed, the system comprising:
a plurality of load detectors each of which is the load detector as defined in any one of items 1 to 10, the plurality of load detectors being disposed under legs of the bed, respectively; and
a controller connected to the plurality of load detectors and configured to calculate the load of the human subject based on an output of the load detector.

What is claimed is:

1. A load detector, comprising:
a load cell which is supported on a support base in a cantilever manner; and
a platform fixed to the load cell,
wherein the platform includes a main body on which a subject is to be placed and a slope having a first end, which is connected to the main body, the slope being configured to guide the subject to the main body,
the slope is configured to swing, relative to the main body,
the platform further includes a lever connected to the first end of the slope and positioned above the main body, and
the lever includes a contact part configured to move by being pushed by the subject on the main body and an arm connecting the contact part and the slope.

2. The load detector according to claim 1, wherein a recess configured to accommodate the lever is provided in an upper surface of the main body.

3. The load detector according to claim 1, wherein the lever includes a movement regulation part configured to regulate movement of the subject placed on the main body.

4. The load detector according to claim 1, wherein the main body includes a plate configured to keep or retain the subject during load detection and a wall provided on the plate.

5. The load detector according to claim 1,
wherein the load cell includes a first load cell which is supported on a first support base in a cantilever manner to have a free end and a second load cell which is disposed to face the first load cell and which is supported on a second support base in a cantilever manner to have a free end,
the platform is provided between the first load cell and the second load cell and further includes a first connection part connected to the first load cell and a second connection part connected to the second load cell,
the free end of the first cell and the free end of the second load cell face opposite directions to each other in an extending direction of the first load cell, and
the first connection part of the platform is connected to the first load cell on a side of the free end of the first load cell and the second connection part of the platform is connected to the second load cell on a side of the free end of the second load cell.

6. The load detector according to claim 5, wherein the first load cell is disposed parallel to the second load cell.

7. A load detector, comprising:
a load cell which is supported on a support base in a cantilever manner; and
a platform fixed to the load cell,
wherein the platform includes a main body on which a subject is to be placed and a slope having a first end, which is connected to the main body, the slope being configured to guide the subject to the main body,
the slope is configured to swing, relative to the main body, between a first position in which a second end of the slope is in contact with a placement surface on which the load detector is placed and a second position in which the second end is separated from the placement surface,
the main body includes an opening, and
the platform further includes a lever connected to the first end of the slope and disposed below the main body to cover the opening.

8. The load detector according to claim 7, wherein the main body includes a plate configured to keep or retain the subject during load detection and a wall provided on the plate.

9. The load detector according to claim 7,
wherein the load cell includes a first load cell which is supported on a first support base in a cantilever manner to have a free end and a second load cell which is disposed to face the first load cell and which is supported on a second support base in a cantilever manner to have a free end,
the platform is provided between the first load cell and the second cell and further includes a first connection part connected to the first load cell and a second connection part connected to the second load cell, the free end of the first load cell and the free end of the second load cell face opposite directions to each other in an extending direction of the first load cell, and the first connection part of the platform is connected to the first load cell on a side of the free end of the first load cell and the second connection part of the platform is connected to the second load cell on a side of the free end of the second load cell.

10. The load detector according to claim 9, wherein the first load cell is disposed parallel to the second load cell.

11. A load detection system configured to detect a load of a human subject on a bed, the system comprising:
a plurality of load detectors each of which is the load detector as defined in claim 1, the plurality of load detectors being disposed under legs of the bed, respectively; and
a controller connected to the plurality of load detectors and configured to calculate the load of the human subject based on an output of the load detector.

12. A load detection system configured to detect a load of a human subject on a bed, the system comprising:
a plurality of load detectors each of which is the load detector as defined in claim 7, the plurality of load detectors being disposed under legs of the bed, respectively; and
a controller connected to the plurality of load detectors and configured to calculate the load of the human subject based on an output of the load detector.

13. A load detector, comprising:
a load cell which is supported on a support base in a cantilever manner; and
a platform connected to the load cell,
wherein the platform includes a main body on which a subject is to be placed and a slope having a first end, which is connected to the main body, the slope being configured to guide the subject to the main body,
the slope is configured to swing between a first position in which a second end of the slope is in contact with a placement surface on which the load detector is placed and a second position in which the second end is separated from the placement surface,
the platform further includes a lever connected to the first end of the slope and positioned above the main body, and
the lever includes a contact part configured to move by being pushed by the subject on the main body and an arm connecting the contact part and the slope.

14. A load detector according to claim 1, wherein the slope is connected at the main body, and the main body is configured such that a load of the subject at the slope acts on the load cell through the main body.

15. A load detector according to claim 1, wherein the main body and the slope are jointly coupled to the load cell and thus jointly configured to at least partially move together relative to the support base.

16. A load detector according to claim 1, wherein the slope is rotatably coupled at the main body.

17. The load detector according to claim 13, wherein a recess configured to accommodate the lever is provided in an upper surface of the main body.

18. The load detector according to claim 13, wherein the lever includes a movement regulation part configured to regulate movement of the subject placed on the main body.

19. The load detector according to claim 13, wherein the main body includes a plate configured to keep or retain the subject during load detection and a wall provided on the plate.

20. The load detector according to claim 13,
wherein the load cell includes a first load cell which is supported on a first support base in a cantilever manner to have a free end and a second load cell which is disposed to face the first load cell and which is supported on a second support base in a cantilever manner to have a free end,
the platform is provided between the first load cell and the second load cell and further includes a first connection part connected to the first load cell and a second connection part connected to the second load cell,
the free end of the first load cell and the free end of the second load cell face opposite directions to each other in an extending direction of the first load cell, and
the first connection part of the platform is connected to the first load cell on a side of the free end of the first load cell and the second connection part of the platform is connected to the second load cell on a side of the free end of the second load cell.

21. The load detector according to claim 20, wherein the first load cell is disposed parallel to the second load cell.

22. A load detection system configured to detect a load of a human subject on a bed, the system comprising:
a plurality of load detectors each of which is the load detector as defined in claim 13, the plurality of load detectors being disposed under legs of the bed, respectively; and
a controller connected to the plurality of load detectors and configured to calculate the load of the human subject based on an output of the load detector.

* * * * *